(12) United States Patent
Liu

(10) Patent No.: US 11,685,757 B2
(45) Date of Patent: Jun. 27, 2023

(54) PHARMACEUTICAL CO-CRYSTAL COMPOSITION AND USE THEREOF

(71) Applicant: SYN-NAT PRODUCTS ENTERPRISE LLC, Potomac, MD (US)

(72) Inventor: Xiaozhong Liu, Potomac, MD (US)

(73) Assignee: SYN-NAT PRODUCTS ENTERPRISE LLC, Potomac, MD (US)

( * ) Notice: Subject to any disclaimer, the term of this patent is extended or adjusted under 35 U.S.C. 154(b) by 65 days.

(21) Appl. No.: 17/122,380

(22) Filed: Dec. 15, 2020

(65) Prior Publication Data

US 2021/0094979 A1 Apr. 1, 2021

Related U.S. Application Data

(63) Continuation of application No. 16/541,504, filed on Aug. 15, 2019, now abandoned, which is a continuation of application No. 15/736,179, filed as application No. PCT/US2016/039572 on Jun. 27, 2016, now Pat. No. 10,428,099.

(60) Provisional application No. 62/184,591, filed on Jun. 25, 2015.

(51) Int. Cl.
| | | |
|---|---|---|
| C07F 15/00 | (2006.01) |
| A61K 9/00 | (2006.01) |
| A61K 33/243 | (2019.01) |
| A61K 35/00 | (2006.01) |
| A61K 31/282 | (2006.01) |
| A61K 45/06 | (2006.01) |
| C07C 61/04 | (2006.01) |
| C07C 61/06 | (2006.01) |
| A61K 47/54 | (2017.01) |
| A61K 9/08 | (2006.01) |
| A61K 47/26 | (2006.01) |
| A61P 35/00 | (2006.01) |

(52) U.S. Cl.
CPC ........ *C07F 15/0093* (2013.01); *A61K 9/0019* (2013.01); *A61K 9/08* (2013.01); *A61K 31/282* (2013.01); *A61K 33/243* (2019.01); *A61K 45/06* (2013.01); *A61K 47/26* (2013.01); *A61K 47/542* (2017.08); *A61P 35/00* (2018.01); *C07C 61/04* (2013.01); *C07C 61/06* (2013.01); *C07B 2200/13* (2013.01)

(58) Field of Classification Search
CPC ..... C07F 15/0093; A61K 9/0019; A61K 9/08; A61K 31/282; A61K 33/243; A61K 45/06; A61K 47/26; A61K 47/542; A61K 33/24; A61K 2300/00; A61K 45/26; A61P 35/00; A61P 31/12; C07C 61/04; C07C 61/06; C07B 2200/13
See application file for complete search history.

(56) References Cited

PUBLICATIONS

Apps, M. G., "The state-of-play and future of platinum drugs." Endocrine-related cancer 22.4 (2015): R219-R233.*
Verweij, M., Preventive Medicine Between Obligation and Aspiration 2013, Springer Science and Business Media Ch. 3; excerpt p. 1-31.*

* cited by examiner

*Primary Examiner* — John M Mauro
(74) *Attorney, Agent, or Firm* — Nixon & Vanderhye, PC

(57) ABSTRACT

The current invention relates to series of co-crystals of platinum analogues and their pharmaceutical use. The co-crystals of the subject invention may be used in the treatment or prevention of cancers and virus infections.

20 Claims, 11 Drawing Sheets

PHARMACEUTICAL CO-CRYSTAL COMPOSITION AND USE THEREOF

CROSS-REFERENCE TO RELATED APPLICATIONS

This application is a Continuation of Ser. No. 16/541,504, filed Aug. 15, 2019, which is a Continuation of Ser. No. 15/736,179, filed Dec. 13, 2017, now U.S. Pat. No. 10,428,099, which is a U.S. National Phase of PCT Application No. PCT/US2016/39572, filed Jun. 27, 2016, which claims the benefit of Provisional Patent Application No. 62/184,591, filed Jun. 25, 2015, each of which is incorporated herein by reference in its entirety.

FIELD OF THE INVENTION

The current invention relates to a series of co-crystals of platinum analogues with diacids and the pharmaceutical use of these co-crystals. The co-crystals of the current invention may be used in the treatment or prevention of various diseases such as cancers and virus infections.

BACKGROUND OF THE INVENTION

The interest in platinum-based antitumor drugs has its origin in the 1960's, with the serendipitous discovery by Rosenberg of the inhibition of cell division by platinum (Pt) complexes. Since the approval of cisplatin for the treatment of testicular and ovarian cancer in 1978, cisplatin has become one of the three most widely utilized antitumor drugs in the world. Platinum-based anticancer drugs have revolutionized cancer chemotherapy, and continue to be in widespread clinical use, especially for management of tumors of the ovary, testes, and the head and neck. Thousands of Pt compounds have been synthesized and evaluated as potential antitumor agents and over 28 have entered human clinical trials. However, several types of dose limiting toxicities associated with platinum drug use, partial anti-tumor response in most patients, development of drug resistance, tumor relapse, and other challenges have severely limited the patient quality of life. Therefore, it is desirable to develop new strategies for improving platinum therapy.

The search continues for an improved Pt antitumor agent. In the years following the introduction of cisplatin, the design of new Pt antitumor drugs focused mainly on direct cisplatin analogues, which adhered to the set of structure-activity relationships summarized by Cleare and Hoeschele in 1973. A number of researchers have taken a completely different approach to Pt drug design and have produced compounds that are inconsistent with the traditional structure-activity relationships but still show antitumor activities.

Carboplatin, one of the second generation platin analogues, is less toxic than cisplatin and can be administered at a significantly higher dose than cisplatin (up to 2000 mg/dose); it has received worldwide approval and has achieved routine clinical use. Unfortunately, the continued use of carboplatin is restricted by severe dose limiting side effects and intrinsic or acquired drug resistance.

In contrast to the 1970s and 1980s, the design of third-generation Pt drugs in the recent years has clearly shifted away from the early empirical structure-activity relationships and the synthesis of mere cisplatin analogues. Instead, efforts have been directed at the design of compounds capable of circumventing specific mechanisms of resistance and at the design of unconventional Pt compounds with radically different modes of action. As the third-generation of compounds undergo clinical trials, it is hoped that they will demonstrate significant clinical advantages over the current drugs, particularly in the area of Pt drug resistance.

Meanwhile co-crystallization has attracted great amount of academic, industrial and therapeutic interests by co-crystallization of two or more pure compounds with crystal engineering to create a new functional material. Specifically, pharmaceutical co-crystals are defined as "co-crystals in which the target molecule or ion is an active pharmaceutical ingredient, API, and it bonds to the co-crystal former(s) through hydrogen bonds." Almarsson M. and Zaworotko J., *Chem. Commun.*, 2004: 1889. Pharmaceutical co-crystals are nonionic supramolecular complexes and can be used to improve physiochemical properties such as solubility, stability and bioavailability in pharmaceutical development without changing the chemical composition of the active pharmaceutical ingredient (API).

Therefore, it is desirable to improve the physiochemical and therapeutic properties of cisplatin, carboplatin and other platin with co-crystallization technology. In some cases, there is no need to change the basic structure of the platin as the API, while properties such as solubility, stability, permeability and bioavailability can be improved. For example, it would be possible to significantly enhance the bioavailability of a platin API with co-crystallization, so that the co-crystal can be therapeutically effective in certain environment of use and maintain the level for a prolonged period of time.

The present invention provides a series of co-crystals including a platinum analogue and a diacid as coformers. The co-crystals of this invention may satisfy one or more of the targeted objectives, such as but not limited to increased solubility, stability and bioavailability and more versatility in pharmaceutical use.

SUMMARY OF THE INVENTION

The present invention provides a series of co-crystals comprising a platinum analogue and a diacid. In some embodiments, co-crystals have a structure of Formula (I):

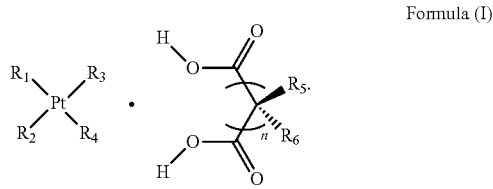

Formula (I)

In some embodiments, the platinum analogue

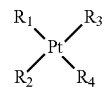

is selected from the structures of formulas from Pt-00 to Pt-33 and SPI-77 listed in Tables 1-5. In some embodiments, the diacid

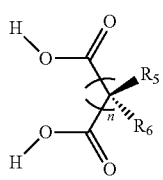

is selected from the structures of formulas CF-01, CF-02, CF-03, CF-04, CF-05, CF-06, CF-07, CF-08, CF-10A, CF-10B, CF-10C and CF-10D listed in Table 6.

In one aspect, the co-crystal of the present invention is formed where the platinum analogue, the active pharmaceutical ingredient (API), and the diacid, the co-crystal former, are bonded together through hydrogen bonds. In some embodiments, other non-covalent interactions may also be in the co-crystal. In one embodiment, other non-covalent and covalent interactions may also be present in the co-crystal.

In another aspect, the present invention provides a pharmaceutical composition comprising the compounds of the co-crystals of Formula I, wherein the co-crystal comprises a platinum analogue and a diacid. In some embodiments of the pharmaceutical composition, the platinum analogue is the API.

One aspect of the invention relates to platinum analogue-based co-crystals which provide a sufficient level of bioavailability to be therapeutically effective in pharmaceutical use and maintains the level for a therapeutically effective period of time.

Another aspect of the invention is to provide uses of the compounds of the co-crystals (e.g. the co-crystals of Formal I) in certain indications; in some embodiments the uses of the compounds of the co-crystals extend beyond the uses of carboplatin by itself. In some embodiments, the present invention relates to treating or preventing a disease in a subject in need thereof comprising administering to the subject the pharmaceutical composition comprising the compound of the co-crystal of Formula I, wherein the compound is in a therapeutically effective amount. In some embodiments, the disease is a cancer; in other embodiments, the disease is a virus infection.

In one aspect, the present invention involves the use of a pharmaceutical composition comprising the compounds of the co-crystal of the current invention to induce cell death in cancer cells by contacting the cancer cells with an effective amount of the compound.

In some embodiments of the treatment of cancers, the therapeutically effective amount of the compound is about 0.01 to about 10 mg/kg body weight, and in some particular embodiments about 0.01 to about 5 mg/kg body weight.

In some embodiments of treatment of virus diseases, the therapeutically effective amount of the compound is about 0.01 to about 10 mg/kg body weight, and in some particular embodiments about 0.01 to 5 mg/kg body weight.

DETAILED DESCRIPTION OF THE INVENTION

Figure 1:
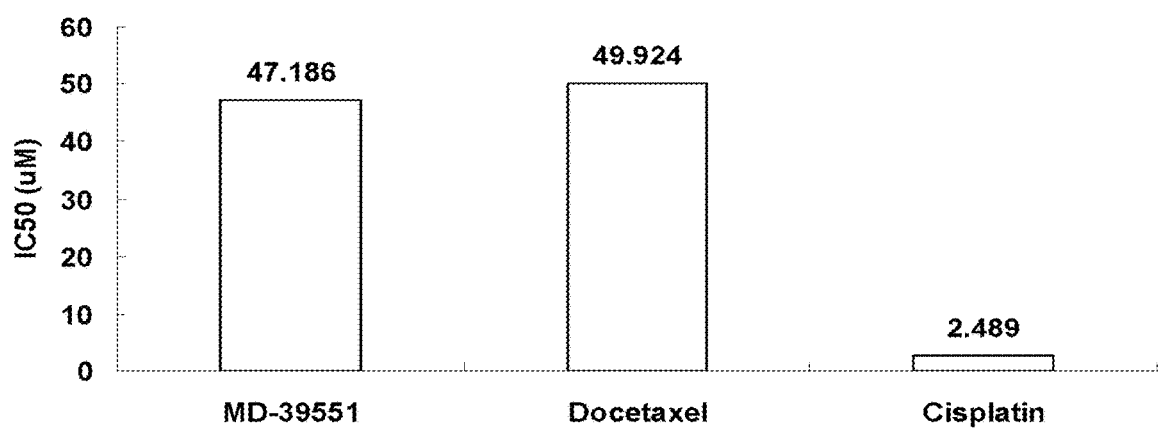
FIG. 1 shows the $IC_{50}$ values of MD-39551 and the control chemicals docetaxel and cisplatin in PC-3 prostate cancer cell line.

The following description of certain embodiment(s) is merely exemplary in nature and is in no way intended to limit the invention, its application, or uses. As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls. Unless defined otherwise, all technical and scientific terms used herein have the same meaning as is commonly understood by one of skill in the art to which this invention belongs. All patents and publications referred to herein are incorporated by reference in their entireties.

The term "effective amount" or "therapeutically effective amount" refers to that amount of a compound or combination of compounds as described herein that is sufficient to effect the intended application including, but not limited to, prophylaxis or treatment of diseases. A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells and/or tissues (e.g., the reduction of cell proliferation and/or morphological alteration of the tissue). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A "prophylactic effect" (e.g. terms such as "prophylaxis," "prevent" and "reducing the likelihood for developing") includes delaying or eliminating the appearance of a disease or condition, delaying or eliminating the onset of symptoms of a disease or condition, slowing, halting, or reversing the progression of a disease or condition, or any combination thereof by administering a drug before the onset of the disease or condition. A "treatment effect" (e.g. with terms such as "treatment" and "treat") includes reducing or eliminating the appearance of a disease or condition, reducing or eliminating the symptoms of a disease or condition, slowing, halting, or reversing the progression of a disease or condition, or any combination thereof by administering a drug after the onset of the disease or condition.

A "subject" as the term is used herein, refers to a human or non-human animal. In some embodiments, the subject is a mammal. In some embodiments, the subject is human.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. In some embodiments, the variation is from 0% to 15%; in some particular embodiments from 0% to 10%; and in other embodiments from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds used in the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Compound of the co-crystal" refers to crystalline and amorphous forms made from the co-crystal, wherein "made from" means left unaltered or processed with known methods such as but not limited to dissolving, condensing, crystalline disruption, drying, grinding, compaction, and polymer film coating. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The present invention relates to a series of co-crystals of platinum analogues, and methods of making and using the same. The co-crystal comprises a platinum analogue and a diacid as coformers. In some embodiments, the co-crystal formula is presented as Formula (I):

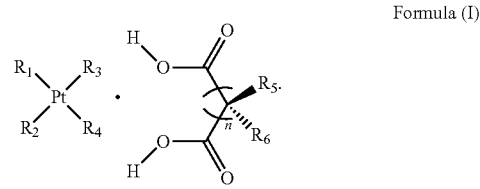

Formula (I)

In some embodiments, the platinum analogue

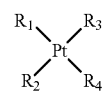

represents the platinum-based anticancer drugs which are approved or already in marketing shown in Table 1.

TABLE 1

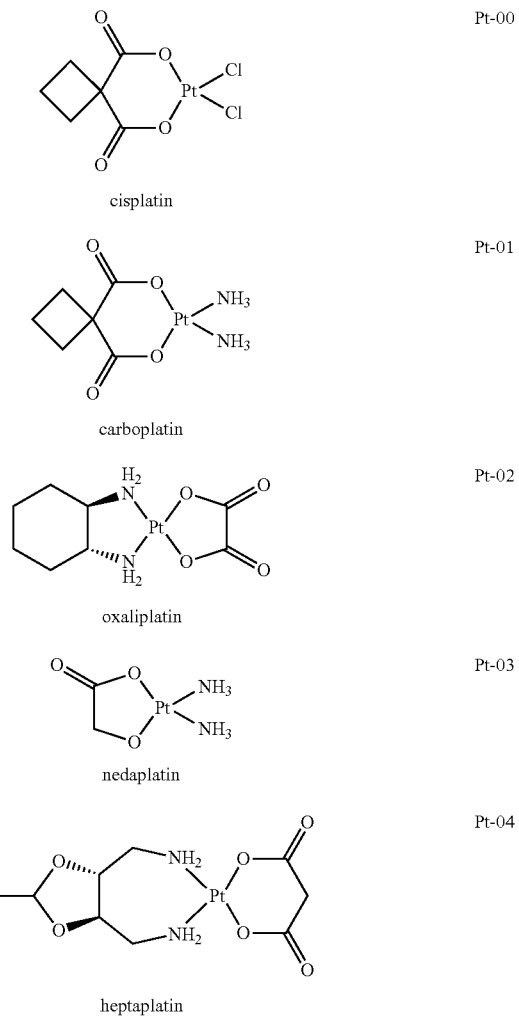

cisplatin — Pt-00 carboplatin — Pt-01 oxaliplatin — Pt-02 nedaplatin — Pt-03 heptaplatin — Pt-04

TABLE 1-continued

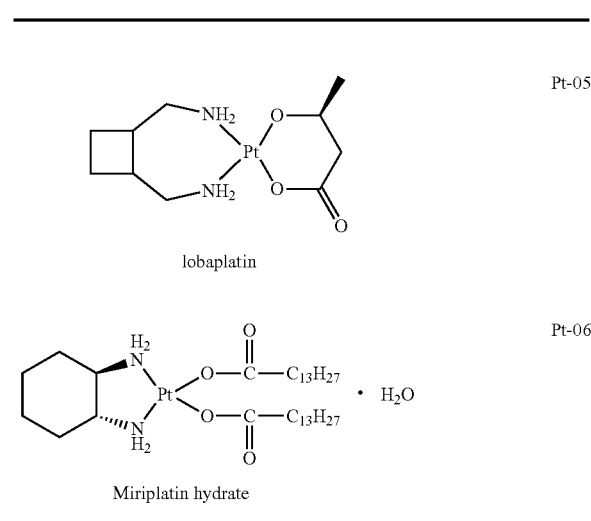

lobaplatin    Pt-05

Miriplatin hydrate    Pt-06

In some embodiments, the platinum analogue

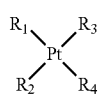

represents lipoplatin and other platinum-based anticancer drugs shown in Table 2.

TABLE 2

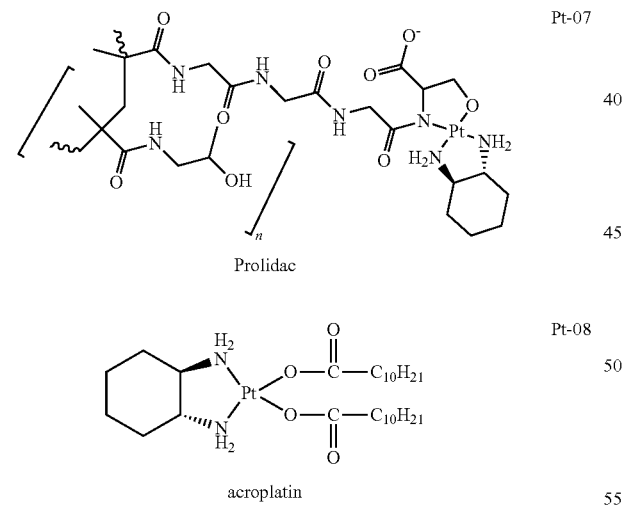

Prolidac    Pt-07 acroplatin    Pt-08

In some embodiments, the platinum analogue

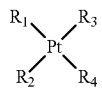

represents the platinum-based anticancer drugs in clinic phases shown in Table 3.

TABLE 3

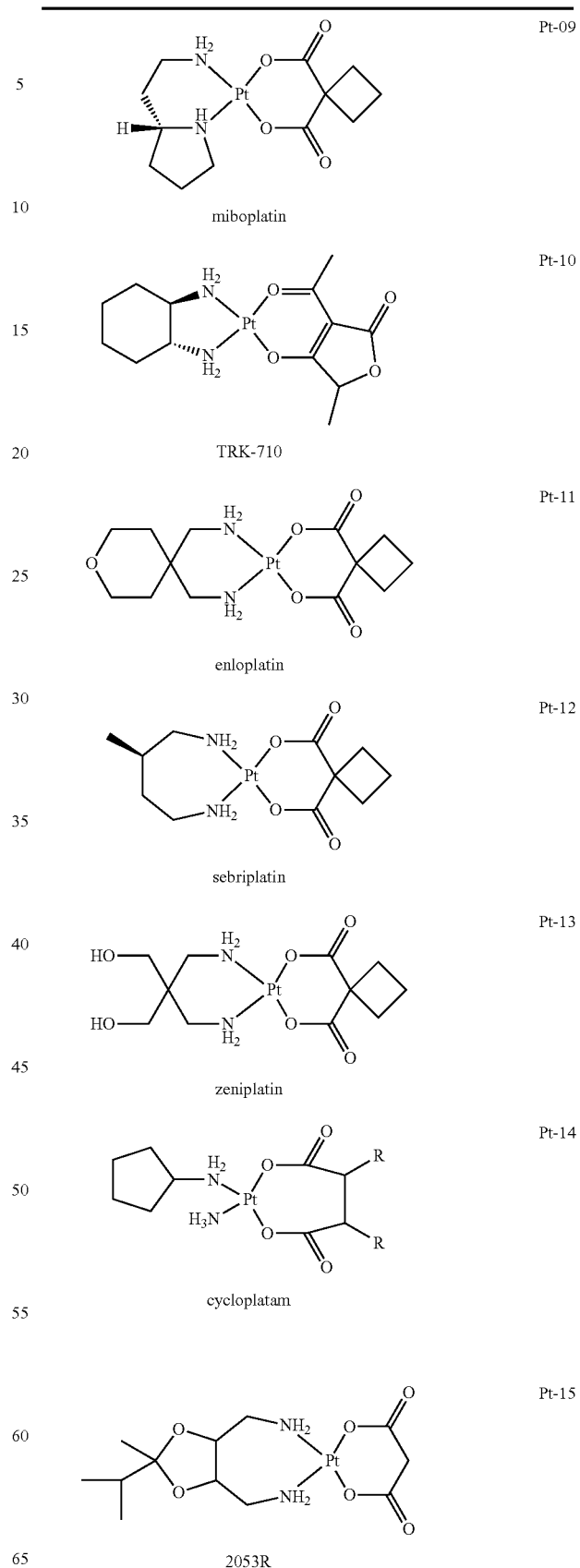

miboplatin    Pt-09

TRK-710    Pt-10 enloplatin    Pt-11 sebriplatin    Pt-12 zeniplatin    Pt-13 cycloplatam    Pt-14

2053R    Pt-15

TABLE 3-continued
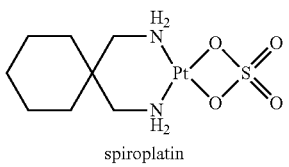
spiroplatin
Pt-16
In some embodiments, the platinum analogue
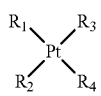
represents the platinum-based anticancer drugs in study as shown in Table 4.
TABLE 4
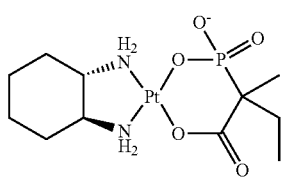
Pt-17
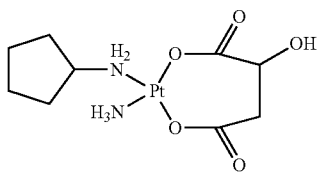
Pt-18
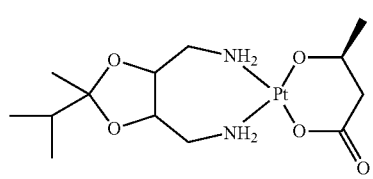
Pt-19
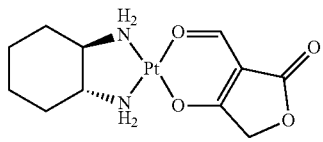
Pt-20
In some embodiments, the platinum analogue
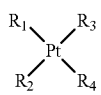
represents the platinum-based structures as shown in Table 5.
TABLE 5
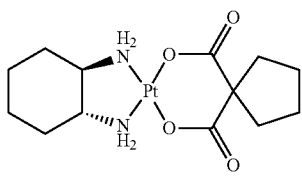
Pt-21
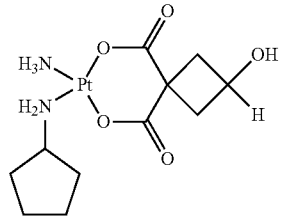
Pt-22
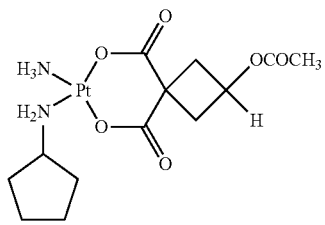
Pt-23
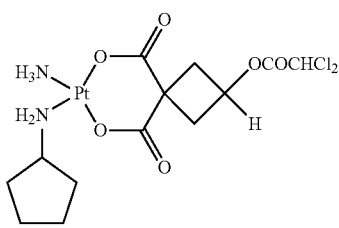
Pt-24
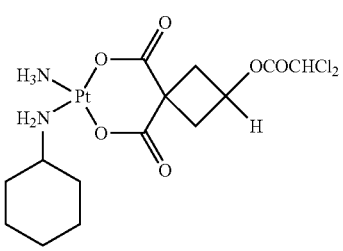
Pt-25
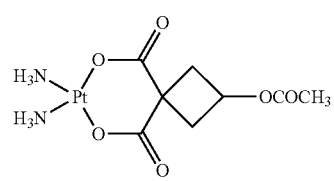
Pt-26
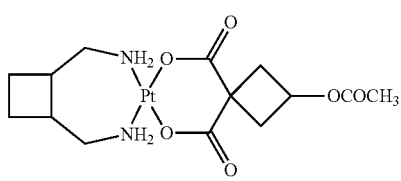
Pt-27

TABLE 5-continued

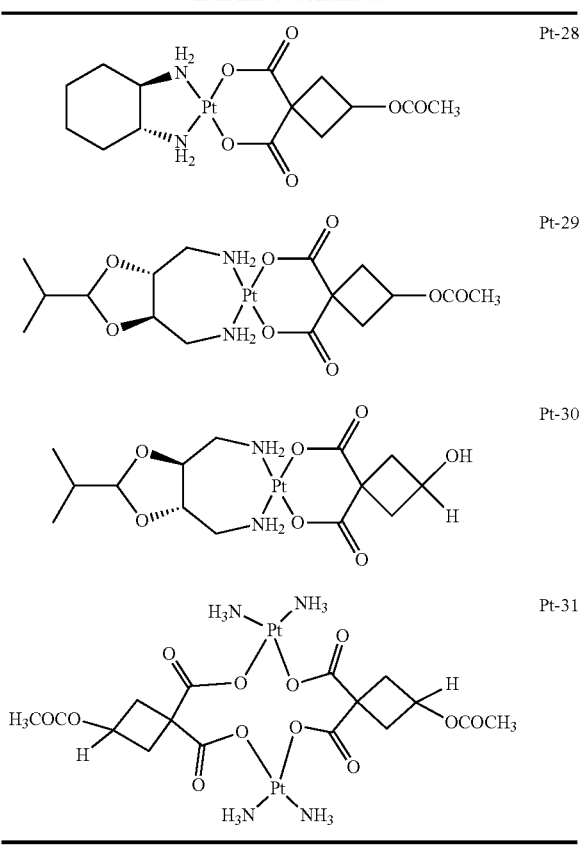

In some embodiments, the platinum analogue

represents the platinum-based anticancer drugs JM11 and iproplatin as disclosed in Wheate, S. et al. *Dalton Trans.*, 2010, Vol. 39, 8113-27. The structure of JM11 and iproplatin are shown below:

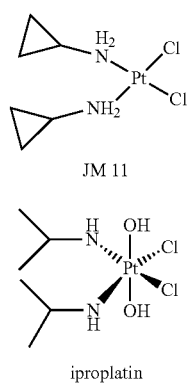

In some embodiments of Formula (I), n is an integer selected from 0 to 5; in some embodiments of Formula (I), n is an integer selected from 2 to 5. In some embodiments, when n≥2, the carbon atoms on the diacid may be connected by single or double bonds.

In some embodiments, the platinum analogue and the diacid are bonded at a 1:1 ratio.

In some embodiments, $R_5$ and $R_6$ are the same as or different from each other, and independently represent a hydrogen, a halogen, an amino group, a C1-C6 alkyl group, a cyanide group, a hydroxyl group, an acyl group, a phosphoryl group, a phosphoroamido group, a hydroxylcarboxyl group, a phenyl group, or an aliphatic group, or R5 and R6 are connected to form a substituted or unsubstituted C3-C6 cycloalkyl group or phenyl group.

In some embodiments, the diacid

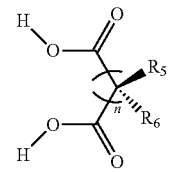

may be selected from the group consisting of oxalic acid, 1,3-propanedioic acid, 1,4-butanedioic acid, 1,5pentanedioic acid, cis-butenedioic acid, 2-hydroxy-1,4-butanedioic acid (malic acid), 2,3-dihydroxy-1,4-butanedioic acid (tartaric acid), 2-phenyl-1,3-propanedioic acid, 1,2-dicarboxycyclohexane, 3-hydroxy-3-carboxy-1,5-pentanedioic acid (citric acid), phthalic acid, and 1,3,4-benzene-ticarboxylic acid.

In some embodiments, the diacid

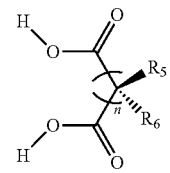

may be selected from formulas CF-01, CF-02, CF-03, CF-04, CF-05, CF-06, CF-07, CF-08, CF-10A, CF-10B, CF-10C and CF-10D in Table 6.

TABLE 6

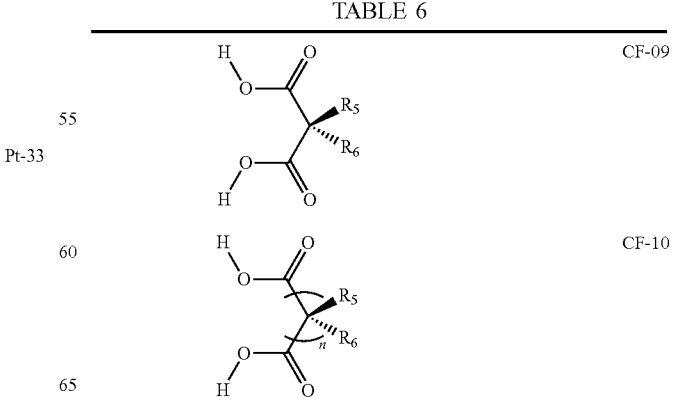

TABLE 6-continued

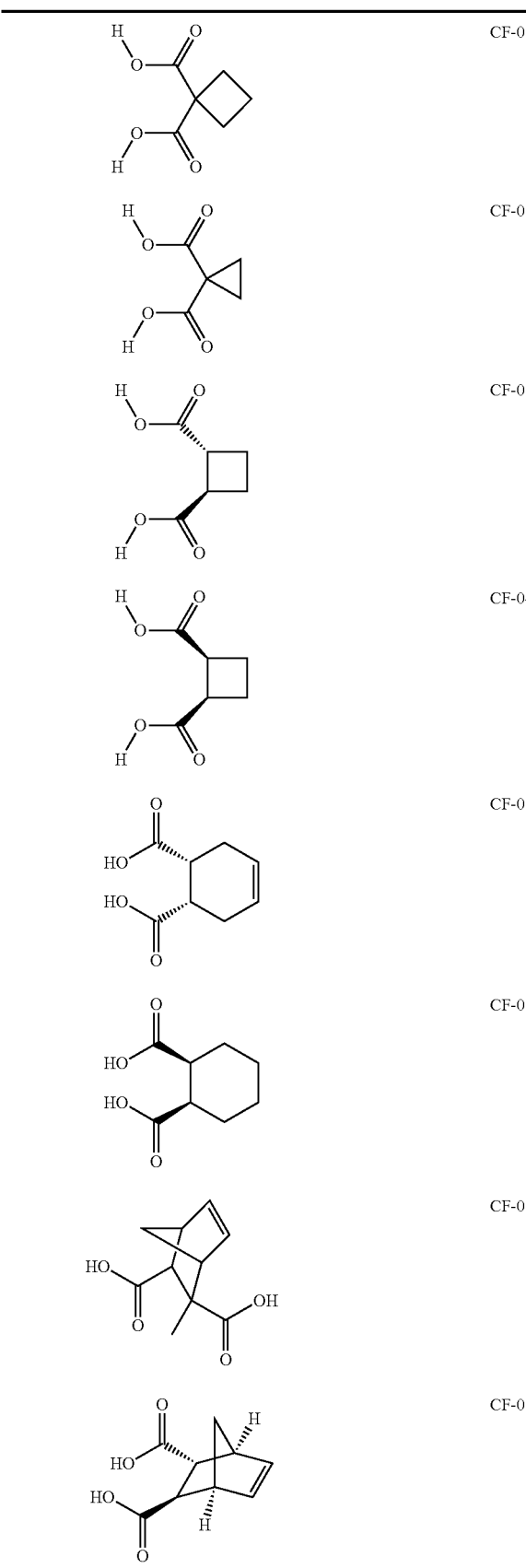

CF-01
CF-02
CF-03
CF-04
CF-05
CF-06
CF-07
CF-08

TABLE 6-continued

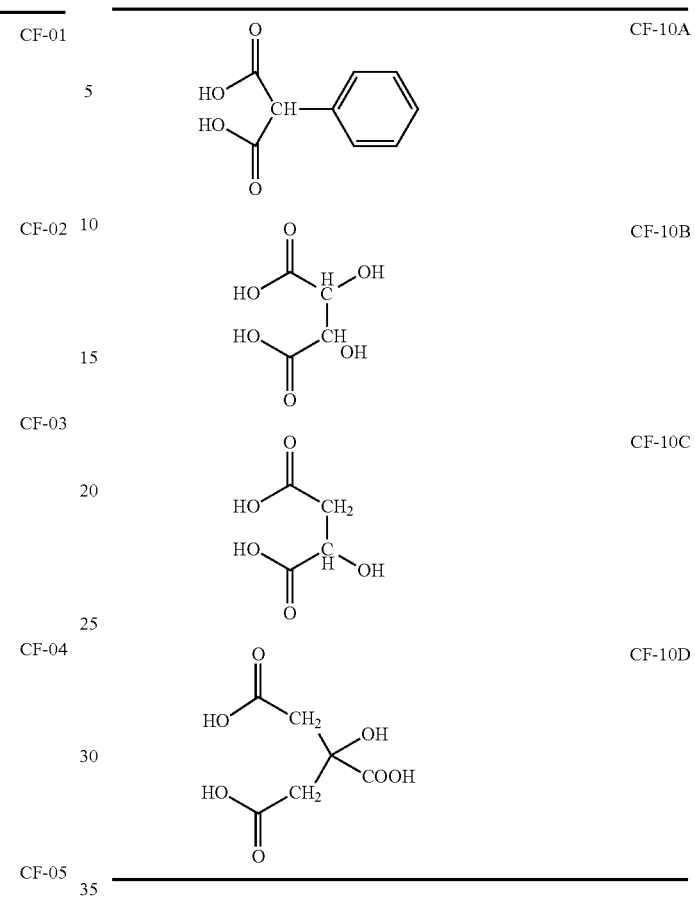

CF-10A
CF-10B
CF-10C
CF-10D

When the platinum analogue is carboplatin (Pt-01), co-crystals disclosed in U.S. Pat. App. Pub. No. 20050160931 and U.S. Pat. No. 6,699,901 are not included in the co-crystals of the present invention. In particular, when the platinum analogue is carboplatin (Pt-01), the diacid does not have the structure of CF-01, CF-04, CF-10A, CF-10B, CF-10C, CF-10D as shown in Table 6.

In some embodiments, the co-crystal of the present invention comprises a platinum analogue selected from the group consisting of formulas Pt-01, Pt-02, Pt-03 and Pt-05.

In some embodiments, the co-crystal of the present invention comprises a diacid selected from the group consisting of formulas CF-01, CF-02, CF-08.

In some embodiments, the co-crystal of the present invention comprises a platinum analogue selected from the group consisting of formulas Pt-01, Pt-02, Pt-03 and Pt-05 and a diacid selected from the group consisting of formulas CF-01, CF-02, CF-08.

In some embodiments, the co-crystal of the present invention comprises the platinum analogue of formula Pt-01 and the diacid of formula CF-02 bonded at 1:1 ratio. In some embodiments, the co-crystal has an XRPD pattern comprising peaks at diffraction angles 2-Theta of 8.821°, 8.961°, 11.998°, 13.160°, 17.681°, 18.001°, 19.101° and 20.837° (round to 8.8°, 9.0°, 12.0°, 13.2°, 17.7°, 18.0°, 19.1° and 20.8°, respectively) (corresponding to d-spacing of 10.0166 Å, 9.8604 Å, 7.3703 Å, 6.7219 Å, 5.0120 Å, 4.9237 Å, 4.6427 Å and 4.2595 Å, respectively)±0.2. In some embodiments, the co-crystal has an XRPD pattern comprising peaks at diffraction angles 2-Theta of 8.821°, 8.961°, 11.998°, 13.160°, 17.681°, 18.001°, 19.101° and 20.837°±0.1. In some embodiments, the co-crystal has an XRPD pattern comprising peaks at diffraction angles 2-Theta of 8.821°, 8.961°, 11.998°, 13.160°, 17.681°, 18.001°, 19.101° and 20.837°±0.05. In some embodiments, the co-crystal has an x-ray diffraction pattern comprising peaks as set forth in FIG. 9. In some embodiments, the co-crystal has an x-ray diffraction pattern substantially similar to the pattern as set forth in FIG. 9.

In some embodiments, the co-crystal of the present invention comprises the platinum analogue of formula Pt-01 and the diacid of formula CF-08 bonded at 1:1 ratio. In some embodiments, the co-crystal has an XRPD pattern comprising peaks at diffraction angles 2-Theta of 6.338°, 14.437°, 14.860°, 15.281°, 19.958°, 22.682° and 24.600° (round to 6.3°, 14.4°, 14.9°, 15.3°, 20.0°, 22.7° and 24.6°, respectively) (corresponding to d-spacing of 13.9342 Å, 6.1301 Å, 5.9567 Å, 5.7936 Å, 4.4451 Å, 3.9171 Å and 3.6158 Å respectively)±0.2. In some embodiments, the co-crystal has an XRPD pattern comprising peaks at diffraction angles 2-Theta of 6.338°, 14.437°, 14.860°, 15.281°, 19.958°, 22.682° and 24.600°±0.1. In some embodiments, the co-crystal has an XRPD pattern comprising peaks at diffraction angles 2-Theta of 6.338°, 14.437°, 14.860°, 15.281°, 19.958°, 22.682° and 24.600°±0.05. In some embodiments, the co-crystal has an x-ray diffraction pattern comprising peaks as set forth in FIG. 11. In some embodiments, the co-crystal has an x-ray diffraction pattern substantially similar to the pattern as set forth in FIG. 11.

Figure 14:
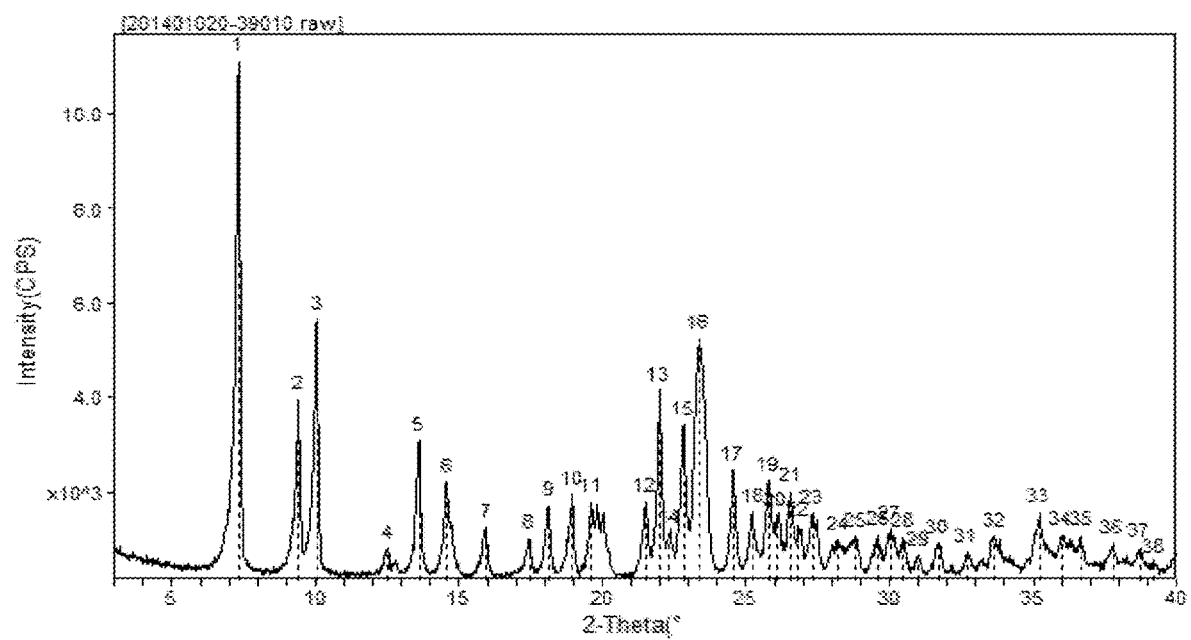
FIG. 14 shows an XRPD pattern of the co-crystal MD-39442.

In some embodiments, the co-crystal of the present invention comprises the platinum analogue of formula Pt-02 and the diacid of formula CF-02 bonded at 1:1 ratio. In some embodiments, the co-crystal has an XRPD pattern comprising peaks at diffraction angles 2-Theta of 7.338°, 9.401°, 10.057°, 12.535°, 13.619° and 23.361° (round to 7.3°, 9.4°, 10.1°, 12.5°, 13.6° and 23.4°, respectively) (corresponding to d-spacing of 12.0363 Å, 9.3993 Å, 8.7877 Å, 7.0557 Å, 6.4967 Å and 3.8048 Å respectively)±0.2. In some embodiments, the co-crystal has an XRPD pattern comprising peaks at diffraction angles 2-Theta of 7.338°, 9.401°, 10.057°, 12.535°, 13.619° and 23.361°±0.1. In some embodiments, the co-crystal has an XRPD pattern comprising peaks at diffraction angles 2-Theta of 7.338°, 9.401°, 10.057°, 12.535°, 13.619° and 23.361°±0.05. In some embodiments, the co-crystal has an x-ray diffraction pattern comprising peaks as set forth in FIG. 14. In some embodiments, the co-crystal has an x-ray diffraction pattern substantially similar to the pattern as set forth in FIG. 14.

In some embodiments, the co-crystal of the present invention comprises the platinum analogue of formula Pt-02 and the diacid of formula CF-01 bonded at 1:1 ratio. In some embodiments, the co-crystal has an XRPD pattern comprising peaks at diffraction angles 2-Theta of 7.079°, 9.180°, and 10.060° (round to 7.1°, 9.2°, and 10.1°, respectively) (corresponding to d-spacing of 12.4769 Å, 9.6252 Å and 8.7856 Å respectively)±0.2. In some embodiments, the co-crystal has an XRPD pattern comprising peaks at diffraction angles 2-Theta of 7.079°, 9.180°, and 10.060°±0.1. In some embodiments, the co-crystal has an XRPD pattern comprising peaks at diffraction angles 2-Theta of 7.079°, 9.180°, and 10.060°±0.05. In some embodiments, the co-crystal has an x-ray diffraction pattern comprising peaks as set forth in FIG. 15. In some embodiments, the co-crystal has an x-ray diffraction pattern substantially similar to the pattern as set forth in FIG. 15.

In some embodiments, the co-crystal of the present invention comprises the platinum analogue of formula Pt-02 and the diacid of formula CF-08 bonded at 1:1 ratio. In some embodiments, the co-crystal has an XRPD pattern comprising peaks at diffraction angles 2-Theta of 7.858°, 11.881°, 14.463°, 15.757°, 16.999°, 17.376° and 17.841° (round to 7.9°, 11.9°, 14.5°, 15.8°, 17.0°, 17.4° and 17.8°, respectively) (corresponding to d-spacing of 11.2418 Å, 7.4427 Å, 6.1193 Å, 5.6194 Å, 5.2115 Å, 5.0993 Å and 4.9676 Å respectively)±0.2. In some embodiments, the co-crystal has an XRPD pattern comprising peaks at diffraction angles 2-Theta of 7.858°, 11.881°, 14.463°, 15.757°, 16.999°, 17.376° and 17.841°±0.1. In some embodiments, the co-crystal has an XRPD pattern comprising peaks at diffraction angles 2-Theta of 7.858°, 11.881°, 14.463°, 15.757°, 16.999°, 17.376° and 17.841°±0.05. In some embodiments, the co-crystal has an x-ray diffraction pattern comprising peaks as set forth in FIG. 17. In some embodiments, the co-crystal has an x-ray diffraction pattern substantially similar to the pattern as set forth in FIG. 17.

Figure 20:
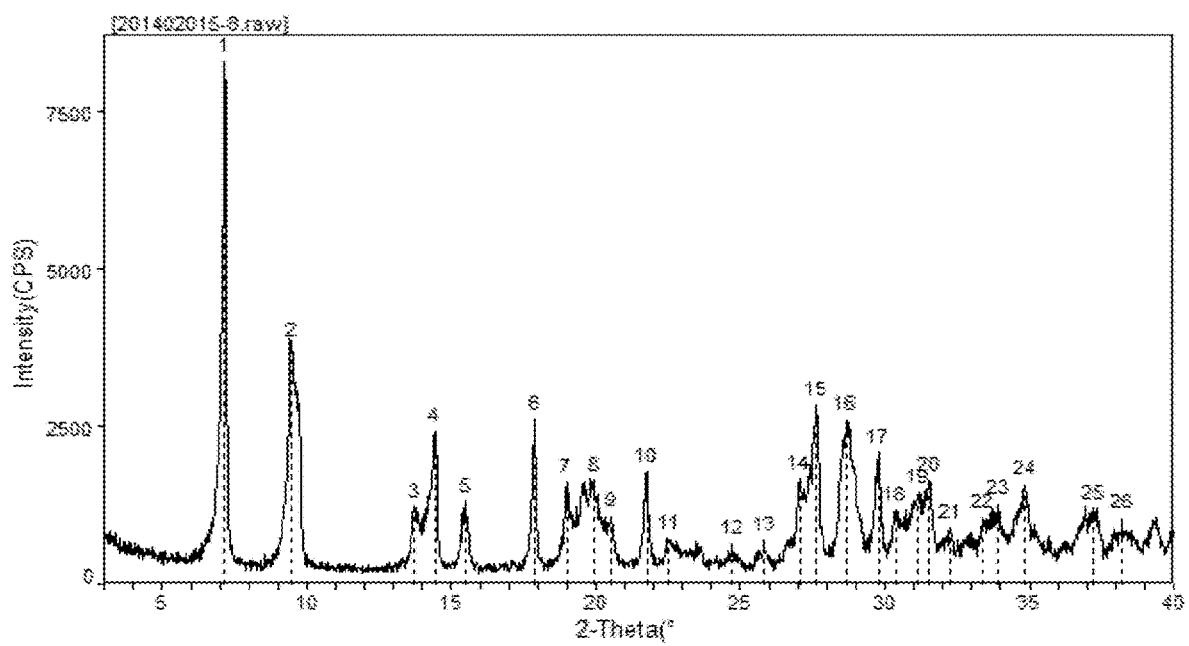
FIG. 20 shows an XRPD pattern of the co-crystal HP-309.

In some embodiments, the co-crystal of the present invention comprises the platinum analogue of formula Pt-03 and the diacid of formula CF-01 bonded at 1:1 ratio. In some embodiments, the co-crystal has an XRPD pattern comprising peaks at diffraction angles 2-Theta of 7.181°, 9.499°, 13.740° and 14.421° (round to 7.2°, 9.5°, 13.7° and 14.4°, respectively) (corresponding to d-spacing of 12.2995 Å, 9.3029 Å, 6.4398 Å and 6.1371 Å respectively)±0.2. In some embodiments, the co-crystal has an XRPD pattern comprising peaks at diffraction angles 2-Theta of 7.181°, 9.499°, 13.740° and 14.421°±0.1. In some embodiments, the co-crystal has an XRPD pattern comprising peaks at diffraction angles 2-Theta of 7.181°, 9.499°, 13.740° and 14.421°±0.05. In some embodiments, the co-crystal has an x-ray diffraction pattern comprising peaks as set forth in FIG. 20. In some embodiments, the co-crystal has an x-ray diffraction pattern substantially similar to the pattern as set forth in FIG. 20.

Figure 21:
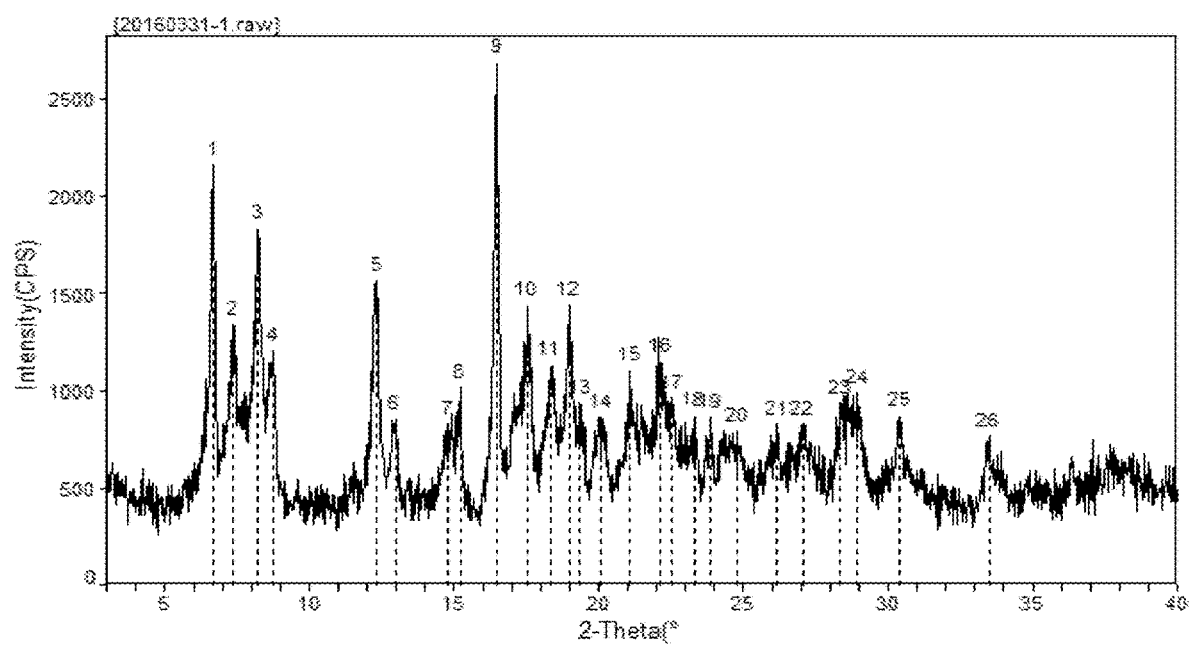
FIG. 21 shows an XRPD pattern of the co-crystal MD3176.

In some embodiments, the co-crystal of the present invention comprises the platinum analogue of formula Pt-05 and the diacid of formula CF-01 bonded at 1:1 ratio. In some embodiments, the co-crystal has an XRPD pattern comprising peaks at diffraction angles 2-Theta of 6.697°, 7.381°, 8.239°, 12.320° and 16.478° (round to 6.7°, 7.4°, 8.2°, 12.3° and 16.5°, respectively) (corresponding to d-spacing of 13.1874 Å, 11.9662 Å, 10.7224 Å, 7.1785A and 5.3751 Å respectively)±0.2. In some embodiments, the co-crystal has an XRPD pattern comprising peaks at diffraction angles 2-Theta of 6.697°, 7.381°, 8.239°, 12.320° and 16.478°±0.1. In some embodiments, the co-crystal has an XRPD pattern comprising peaks at diffraction angles 2-Theta of 6.697°, 7.381°, 8.239°, 12.320° and 16.478°±0.05. In some embodiments, the co-crystal has an x-ray diffraction pattern comprising peaks as set forth in FIG. 21. In some embodiments, the co-crystal has an x-ray diffraction pattern substantially similar to the pattern as set forth in FIG. 21.

In some embodiments, the co-crystal of the present invention comprises: (i) a diacid as a co-former; and (ii) a platinum analogue as a co-former and the active pharmaceutical ingredient (API). In some embodiments, the diacid and the platinum analogue are bonded in 1:1 ratio.

As described here, the solid state of the co-crystal of the current invention is any crystalline polymorphic forms or a mixture thereof. The co-crystal may also be made into an amorphous form, which may be combined with any crystalline forms. In other embodiments, the solid state of the co-crystal is an amorphous form. Different forms of the co-crystal of the current invention may be obtained through different crystallization process and the co-crystals may be made into amorphous forms with known technology.

The compound of the co-crystals of the current invention (e.g. co-crystals of formula I) may demonstrate a sufficient level of bioavailability to be therapeutically effective in pharmaceutical use and maintains that level in a subject for a prolonged period of time.

The co-crystals of the current invention may be produced by a process comprising: (i) providing and mixing a platinum analogue, a diacid and an appropriate solvent, (ii) slurrying or stirring the mixture from step i) for a sufficient period of time; and (iii) isolating the co-crystal formed thereby. In some embodiments, the reaction of the platinum analogue and the diacid may be carried out 30° C. In some embodiments, the mixture after the reaction may be cooled to 0-5° C. and stirred.

The specific conditions of the process may be adjusted to ensure optimized purity, quantity, and/or physiochemical properties. In some embodiments, the proper ratio is in the molar range of 1:0.1-1:20, 1:0.2-1:20, 1:0.3-1:20, 1:0.4-1:20, 1:0.5-1:20, 1:0.6-1:20, 1:0.7-1:20; 1:0.8-1:20, 1:0.9-1:20, 1:1-1:1.20, 1:2-1:20, 1:3-1:20, 1:4-1:20, 1:5-1:20, 1:6-1:18, 1:7-1:15, 1:8-1:13, 1:9-1:12, or 1:10-1:11. In some embodiments, the proper ratio is about 1:1 (molar). In some embodiments, the period of time for slurrying or stirring the mixtures may be in the range of 0.1-24 hours, 0.2-12 hours, 0.25-6 hours, 0.3-2 hours, 0.4-1 hour, or 0.5-1 hour. In some embodiments, the period of time for slurrying or stirring the mixtures may be about 0.5 hour. In some embodiments, the co-crystal compound may be obtained by drying, filtering, centrifugation, pipetting, or a combination thereof. In some embodiments, the co-crystal compound may be obtained by centrifugation.

In some embodiments, the reaction of the platinum analogue and the diacid may be carried out 30° C. In some embodiments, the mixture after the reaction may be cooled to 0-5° C. and stirred.

The current invention relates to the pharmaceutical use of compounds of the co-crystals of the present invention, and methods of treating or preventing a disease in a subject in need thereof. In some embodiments, the method comprises administering to the subject a pharmaceutical composition comprising a therapeutically effective amount of a compound of one or more of the co-crystals of the present invention.

In some embodiments, the compound of the co-crystal of the current invention demonstrates advantageous therapeutic properties. For example, in some embodiments, the compound of the co-crystals of the present invention may be more effective in killing cancerous or virus-infected cells compared to carboplatin or other known drugs. In other embodiments, the compound of the co-crystals of the present invention may be less effective in killing cancerous or virus-infected cells compare to carboplatin or other known drugs or have substantially similar effects, but are less toxic to healthy and normal cells, resulting in a net health benefit. For instance, comparing to know platin analogues in the treatment of cancer cells or virus-infected cells, a compound of the MD39551 (as shown in Table 7) co-crystal may be less toxic and more stable than cisplatin and carboplatin. In addition, a compound of the MD39433 or MD39703 (as shown in Table 7) co-crystals may be less toxic and more stable than oxaliplatin and carboplatin. In some embodiments, the compounds of MD39551, MD39433 or MD39703 may provide reduced side effects. In some embodiments, the compounds of MD39551, MD39433 or MD39703 may demonstrate more versatility in pharmaceutical uses, e.g. when compared to carboplatin.

In some embodiments, the compound of the carboplatin-based co-crystal of the current invention demonstrates advantageous physiochemical properties. For example, in some embodiments, compounds of MD39551, MD39433 or MD39703 may have increased solubility, stability, and bioavailability. For example, in comparison with carboplatin, the compounds of MD39551, MD39433 or MD39703 may be more stable and could be stable in solid form of various doses. Meanwhile, water solubility of compounds of MD39551, MD39433 or MD39703 may be higher than carboplatin, providing significantly more possibility of formulations and administration.

In some embodiments, the pharmaceutical composition may consist of the compounds of the co-crystals of the present invention. In some embodiments, the pharmaceutical composition may comprise the compounds of the co-crystals of the present invention and at least one additional therapeutic agent or adjuvant therapy agent. The additional therapeutic agent or adjuvant therapy agent may be selected from but is not limited to: folic acid, coenzyme Q10, curcumin, glutathione (GSH), aloe vera, oryzanol, 5-fluorouracil, bortezomib, or a combination thereof. Depending on the particular disease to be treated, the additional therapeutic agent or adjuvant therapy agent may include drugs already known. In some embodiments, the additional therapeutic agent or adjuvant therapy agent may include drugs that have already been clinically accepted to treat or prevent the disease.

In some embodiments, the pharmaceutical composition may comprise the compounds of the co-crystals of the present invention and a pharmaceutically acceptable carrier or excipient. "Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

In yet another aspect, the amount of the compound of the co-crystals of the present invention in the pharmaceutical composition administered to a subject may be about 0.005 to 20 mg/kg body weight, about 0.005 to 10 mg/kg body weight, about 0.005 to 5 mg/kg body weight, about 0.005 to 2.5 mg/kg body weight, 0.01 to 20 mg/kg body weight, about 0.01 to 10 mg/kg body weight, about 0.01 to 5 mg/kg body weight, about 0.01 to 2.5 mg/kg body weight, 0.1 to 20 mg/kg body weight, about 0.1 to 10 mg/kg body weight, about 0.1 to 5 mg/kg body weight, or about 0.1 to 2.5 mg/kg body weight. The specific amount of the compound depends on the particular disease to be treated and the subject's specific conditions.

In yet another aspect, the administration of the pharmaceutical composition comprising the compounds of the co-crystals of the present invention may last at least 1, 2, 3, 4, 5, 6, 7, 8, 9, 10, 11, 12, 13, 14, 21, 28, 35, 42, 49, 56, 63, 70, 77, 84, 91 or 98 days. In some embodiments, the administering of the pharmaceutical composition may last at least one week. In some embodiments, the administering of the pharmaceutical composition may last at least two weeks.

The specific period of administration depends on the particular disease to be treated and the subject's specific conditions.

The present invention in various aspects and embodiments involves uses of the co-crystals of the present invention for the prevention or treatment of various diseases and methods of treating or preventing the diseases by administering a pharmaceutical composition comprising the compounds of the co-crystals of the present invention. The diseases to be treated or prevented include but are not limited to cancers and viral infections. For example, the co-crystals may be MD39551, MD39433 or MD39703.

In some embodiments, the disease is a cancer. In some embodiments, the cancer is selected from: bladder cancer, non-small cell lung cancer, cervical cancer, anal cancer, pancreatic cancer, squamous cell carcinoma including head and neck cancer, renal cell carcinoma, basal-cell skin cancer (BCC), squamous-cell skin cancer (SCC), melanoma, ovarian cancer, small cell lung cancer, endometrial cancer, glioblastoma, astroycytoma, oligodendroglioma, ependymoma, neurofibrosarcoma, meningioma, gastrointestinal stromal tumor, breast cancer, lung cancer, colorectal cancer, thyroid cancer, bone sarcoma, stomach cancer, oral cavity cancer, oropharyngeal cancer, gastric cancer, renal adenocarcinoma, liver cancer, prostate cancer, esophageal cancer, testicular cancer, gynecological cancer, colorectal cancer, brain cancer, leukemia, leucocythemia, chronic lymphocytic leukemia (CLL), small lymphocytic leukemia (SLL), non-Hodgkin's lymphoma (NHL), diffuse large B cell lymphoma (DLBCL), follicular lymphoma (FL), mantle cell lymphoma (MCL), Hodgkin's lymphoma, B cell acute lymphoblastic leukemia (B-ALL), Burkitt's lymphoma, Waldenström's macroglobulinemia (WM), Burkitt's lymphoma, multiple myeloma, and myelofibrosis.

In some embodiments, the pharmaceutical composition comprising the compound of the co-crystals of the present invention may be used to prevent or treat prostate cancer, colorectal cancer, or renal adenocarcinoma. In some embodiments, the therapeutically effective amount of the co-crystals of the present invention to prevent or treat cancer may about 0.01 to about 10 mg/kg body weight. In another embodiment, the therapeutically effective amount of the compound of the co-crystals of the present invention to prevent or treat cancer is about 0.01 to about 5 mg/kg body weight.

In some embodiments, the disease is a viral infection. In some embodiments, the virus is a DNA virus or an RNA virus. For example, in some embodiments the virus may be a DNA virus such as but not limited to adenovirus, herpes simplex virus, human pepillomavrus, VITAMIN K virus, smallpox virus, hepatitis B virus (HBV), and parvovirus B19. In other embodiments, the virus may be an RNA virus such as but not limited to human astrovirus, norwalk virus, hepatitis A virus (HAV), severe acute respiratory syndrome virus, hepatitis C virus (HCV), yellow fever virus, dengue virus, West Nile virus, TBE virus, rubella virus, hepatitis E virus (HEV), human immunodeficiency virus (HIV), influenza virus, Lassa virus (LASV), Crimean-Congo hemorrhagic fever virus, Hantaan virus, Ebola virus, Marburg virus, Measles virus, mumps virus, parainfluenza virus, respiratory syncytial virus, rabies virus, and hepatitis D virus (HDV), rotavirus, orbivirus, coltivirus, Banna virus.

In some embodiments, the pharmaceutical composition may be used to prevent or treat viral infections caused by HBV, HCV, HIV or Hantaan virus. In some embodiments, the therapeutically effective amount of the compound of the co-crystals of the present invention to prevent or treat viral infection is about 0.01 to about 10 mg/kg body weight. In another embodiment, the therapeutically effective amount of the compound of the co-crystals of the present invention to prevent or treat cancer is about 0.01 to about 5 mg/kg body weight.

In some embodiments, the present invention provides a method of treating, preventing, reducing or alleviating the symptoms of, and/or slowing or halting the progress of prostate cancer, colorectal cancer, renal adenocarcinoma or leucocythemia in a subject in need thereof, the method comprising administrating to the subject an effective amount of a pharmaceutical composition comprising the compound of the co-crystals of the present invention. In some embodiments, the pharmaceutical composition consists of the compound of the co-crystals of the present invention. In some embodiments, the pharmaceutical composition further comprises at least one additional therapeutic agent or adjuvant therapy agent. In a specific embodiment, the additional therapeutic agent or adjuvant therapy agent may be selected from: folic acid, coenzyme Q10, curcumin, glutathione (GSH), aloe vera, oryzanol, 5-fluorouracil, and bortezomib. In some embodiments, the pharmaceutical composition comprises the compound of the co-crystals of the present invention and a pharmaceutically acceptable carrier or excipient.

In some embodiments, the present invention provides a method of treating, preventing, reducing or alleviating the symptoms of, and/or slowing or halting the progress of prostate cancer, the method comprising administrating to the subject an effective amount of a pharmaceutical composition comprising the compound of co-crystal MD39551.

In some embodiments, the present invention provides a method of treating, preventing, reducing or alleviating the symptoms of, and/or slowing or halting the progress of colorectal cancer, the method comprising administrating to the subject an effective amount of a pharmaceutical composition comprising the compound of co-crystal MD39433 or MD39703.

In some embodiments, the present invention provides a method of treating, preventing, reducing or alleviating the symptoms of, and/or slowing or halting the progress of viral infections caused by HBV, HCV, HIV or Hantaan virus in a subject in need thereof, the method comprising administrating to the subject an effective amount of a pharmaceutical composition comprising the compound of the co-crystals of the present invention. In some embodiments, the pharmaceutical composition consists of the compound of the co-crystals of the present invention. In some embodiments, the pharmaceutical composition further comprises at least one additional therapeutic agent or adjuvant therapy agent. In a specific embodiment, the additional therapeutic agent or adjuvant therapy agent may be selected from: folic acid, coenzyme Q10, curcumin, glutathione (GSH), aloe vera, oryzanol, 5-fluorouracil, and bortezomib. In some embodiments, the pharmaceutical composition comprises the compound of the co-crystals of the present invention and a pharmaceutically acceptable carrier or excipient.

In some embodiments, the administration of the pharmaceutical composition according to the present invention can be via any common route as long as the target issue is available via the route. Suitable routes may include oral, buccal, by inhalation spray, sublingual, rectal, transdermal, vaginal, transmucosal, topical, nasal or intestinal administration; parenteral delivery, including intramuscular, subcutaneous, intramedullary injections, as well as intrathecal, direct intraventricular, orthotopic, intradermal, intraperitoneal, intravenous, intra-articular, intra-sternal, intra-synovial, intra-hepatic, intralesional, intracranial, intraperitoneal, intranasal, or intraocular injections or other modes of delivery. The preferred delivery route depends on the particular disease to be treated and the subject's specific conditions.

In some embodiments, for prevention or treatment of prostate cancer, colorectal cancer, renal adenocarcinoma or leucocythemia, the pharmaceutical composition comprising the compound of the co-crystals of the present invention is administered with infusion, injections or via the oral route. In some embodiments, for prevention or treatment of prostate cancer, colorectal cancer, renal adenocarcinoma or leucocythemia, the pharmaceutical composition comprising the compound of the co-crystals of the present invention is administered for at least one, two or three weeks.

In some embodiments, for prevention or treatment of viral infections caused by HBV, HCV, HIV or Hantaan virus, the pharmaceutical composition comprising the compound of the co-crystals of the present invention is administered with infusion, injections or via the oral route. In some embodiments, for prevention or treatment of viral infections caused by HBV, HCV, HIV or Hantaan virus, the pharmaceutical composition comprising the compound of the co-crystals of the present invention is administered for at least one, two or three weeks.

EXAMPLES

The effects of the co-crystal of the present invention on certain diseases are shown in the following example. In addition, the process of making the co-crystals of the present invention and the physiochemical properties of these crystals are also described. These examples do not in any way limit the scope of the invention.

A number of co-crystals are produced by mixing a platinum analogue with a diacid. The resulting co-crystals meet partly or completely the targeted objectives, such as increased solubility, stability and bioavailability and more versatile in pharmaceutical use compared to carboplatin or other platin compounds.

In comparison with carboplatin, the co-crystal of the current inventions is more stable and can be stable in solid forms. In comparison to the reported platin analogues for the treatment of cancer cells, some of the co-crystals of the current inventions are less toxic and much stable than cisplatin and carboplatin.

The inventors have determined that the formation of crystalline polymorphic forms was confirmed with various methods such as but not limited to XRPD, HPLC, $^1$H-NMR; DSC and SEM. Amorphous forms of the co-crystal and other forms may be existent using different crystallization process.

The Effects of MD-39551 on Prostate Cancer Cells

The co-crystal MD-39551, which comprises the platinum analogue of formula Pt-01 and the diacid of formula CF-08 bonded at 1:1 ratio, was tested in the treatment of prostate cancers and compared to docetaxel and cisplatin, widely accepted drugs for prostate cancer patients.

PC-3 cells are a cell line derived from advanced prostate cancer patient with bone metastasis and are characteristic of prostate cancer such as prostate small cell carcinoma. PC-3 cells were treated with drugs (MD-39551, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 1.

The $IC_{50}$ of MD-39551 was 47.186 µM, while $IC_{50}$ of docetaxel and cisplatin were 49.924 µM and 2.489 µM respectively (FIG. 1).

LNCaP cells are a cell line derived from advanced prostate cancer patient with lymph node metastasis. LNCaP cells were treated with drugs (MD-39551, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 2.

Figure 2:
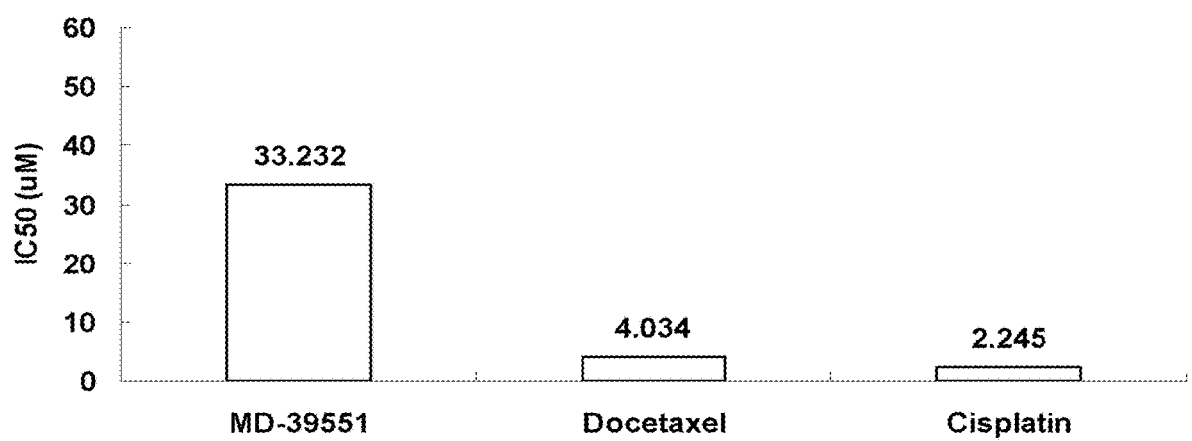
FIG. 2 shows the $IC_{50}$ values of MD-39551 and the control chemicals docetaxel and cisplatin in LNCaP prostate cancer cell line.

For LNCaP cells, the $IC_{50}$ of MD-39551 was 33.232 µM, the $IC_{50s}$ of docetaxel and cisplatin were 4.034 µM and 2.245 µM respectively (FIG. 2).

Figure 3:
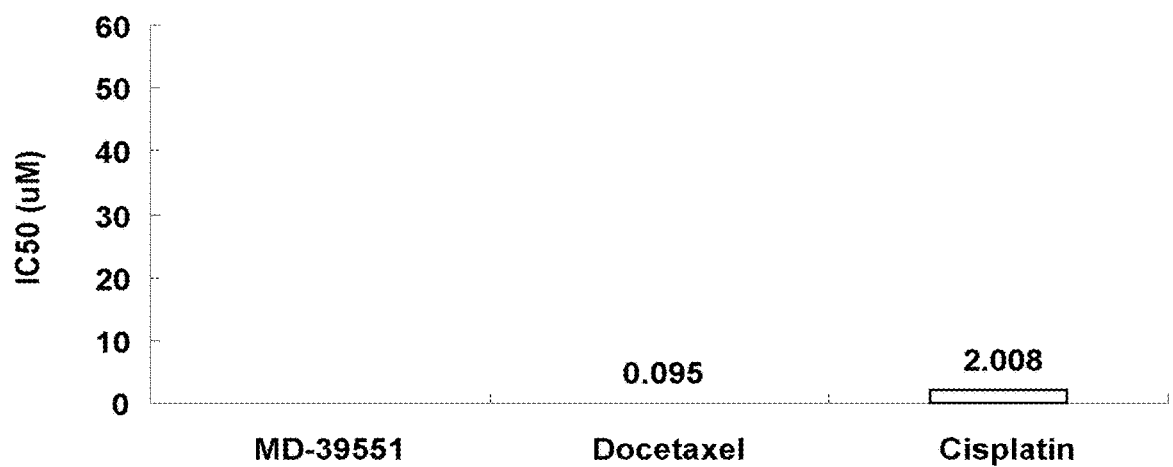
FIG. 3 shows the $IC_{50}$ values of MD-39551 and the control chemicals docetaxel and cisplatin in fetal hepatocytes HL-7002.

HL-7002 cells are an immortalized human fetal hepatic cell line. HL-7002 cells were treated with drugs (MD-39551, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 3.

For HL-7002 cells, while no MD-39551 toxicity was detected, docetaxel and cisplatin showed significant toxicity. The $IC_{50}$ of docetaxel and cisplatin were 0.095 µM and 2.008 µM respectively (FIG. 3).

Figure 4:
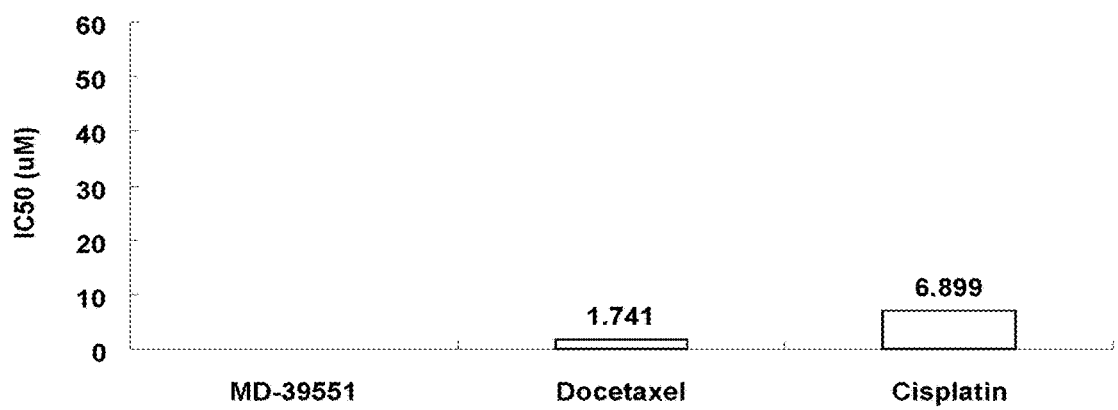
FIG. 4 shows the $IC_{50}$ values of MD-39551 and the control chemicals docetaxel and cisplatin in human embryonic kidney cell line HEK293.

HEK293 cells are an immortalized human fetal kidney cell line. HEK293 cells were treated with drugs (MD-39551, docetaxel, or cisplatin) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 4.

For HEK293 cells, while no MD-39551 toxicity was detected, docetaxel and cisplatin showed significant toxicity. The $IC_{50}$ of docetaxel and cisplatin were 1.741 µM and 6.899 µM, respectively (FIG. 4.).

Methods and Strategies:

Cell culture: Prostate cancer cell lines LNCaP and PC-3 were purchased from ATCC (Manassas, Va.). The fetal hepatocytes HL-7002 and human embryonic kidney cells HEK393 were purchased from ATCC. The cells were cultured in RPMI+5% Fetal Bovine Serum (FBS).

Drug treatment and cell viability (MTS) assay: The cells (105/100 mL/well) were cultured in a 96 well plate, and treated with drugs (e.g. MD-39551) at step-wise concentrations from 0.01 to 300 µM. The cells treated with the solvents were used as the negative control, and cisplatin and docetaxel were used as the positive controls. The cells were monitored daily, and the cell viability was evaluated with the Promega CellTiter 96 AQueous One Solution Cell Proliferation Assay (Promega, Madison, Wis., USA) according to the manufacture manuals. The cell viability was monitored at OD490 reading in a bio-spectrometer (Perkin Elmer, Walthan, Mass., USA).

Data analysis: The OD490 reading data were collected hourly from 1 h to 4 h after the addition of lysis buffer. The index of cell growth repression ratio was obtained by comparing the OD490 data of treatment to the negative control. The drug response rate $IC_{50}$ was calculated with the SPSS 16.0.

Summary of Effects:

For PC-3, a cell line derived from advanced prostate cancer patient with bone metastasis, MD-39551 showed similar cellular toxicity to docetaxel, but weaker than for Cisplatin. For LNCaP, a cell line derived from advanced prostate cancer patient with lymph node metastasis, the cellular toxicity of MD-39551 was weaker than docetaxel and cisplatin. For HL-7002 and HEK293 cells, which respectively represent normal human hepatic cells and kidney cells, while MC-39551 showed no toxicity, both docetaxel and cisplatin demonstrated high toxicity.

The Effects of MD-39703 and MD-39433 on Colorectal Cancer Cells

The co-crystals MD-39703 and MD-39433 was tested in the treatment of colorectal cancers in comparison to oxaliplatin and fluorouracil (5-FU), widely used drugs in treating colorectal cancer patients. MD-39703 comprises the platinum analogue of formula Pt-02 and the diacid of formula CF-08 bonded at 1:1 ratio; MD-39433 comprises the platinum analogue of formula Pt-02 and the diacid of formula CF-01 bonded at 1:1 ratio.

Figure 5:
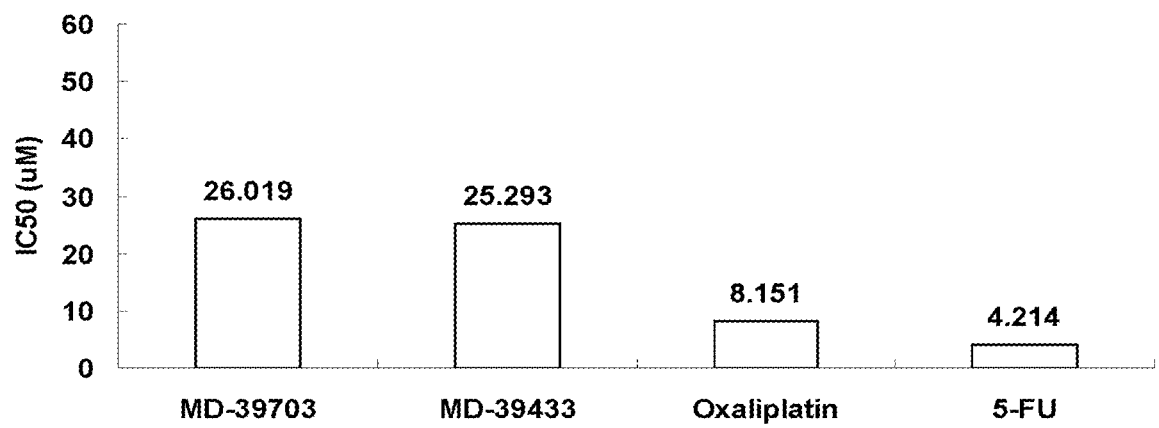
FIG. 5 shows the $IC_{50}$ values of MD-39703 and MD-39433 and the control chemicals oxaliplatin and 5-FU in colorectal cancer cell line HCT-116.

HCT-116 cells are a colorectal cancer cell line. HCT-116 cells were treated with drugs (MD-39703, MD-39433, oxaliplatin, or 5-FU) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 5.

For the reduction of HCT-116 cell number, the $IC_{50}$ of MD-39703 was 26.019 μM and $IC_{50}$ of MD-39433 was 25.293; $IC_{50s}$ of oxaliplatin and 5-FU were be 8.151 μM and 4.214 μM respectively (FIG. 5).

Figure 6:
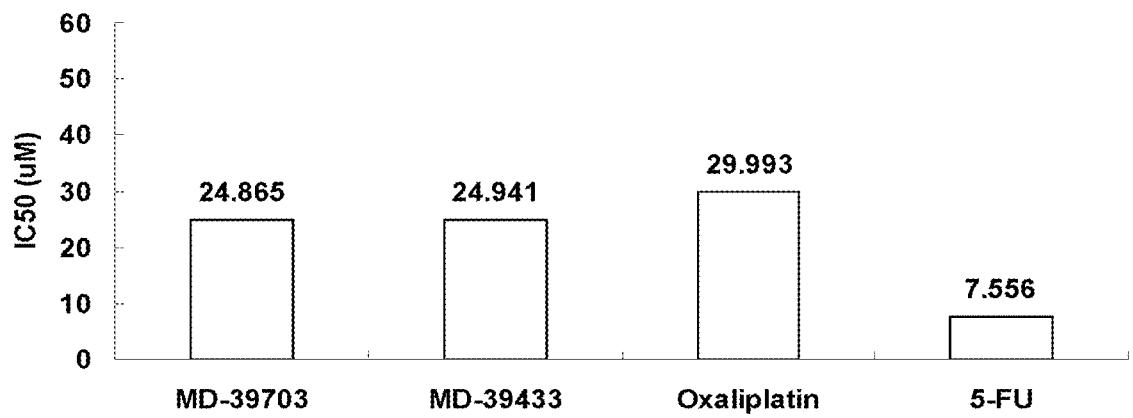
FIG. 6 shows the $IC_{50}$ values of MD-39703 and MD-39433 and the control chemicals oxaliplatin and 5-FU in colorectal cancer cell line HT-29.

HT29 cells are a colorectal cancer cell line. HT29 cells were treated with drugs (MD-39703, MD-39433, oxaliplatin, or 5-FU) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 6.

For HT29 cells, the $IC_{50}$ of MD-39703 was 24.865 μM and $IC_{50}$ of MD-39433 was 24.941; $IC_{50}$, of oxaliplatin and 5-FU were determined to be 29.993 μM and 7.556 μM respectively (FIG. 6).

Figure 7:
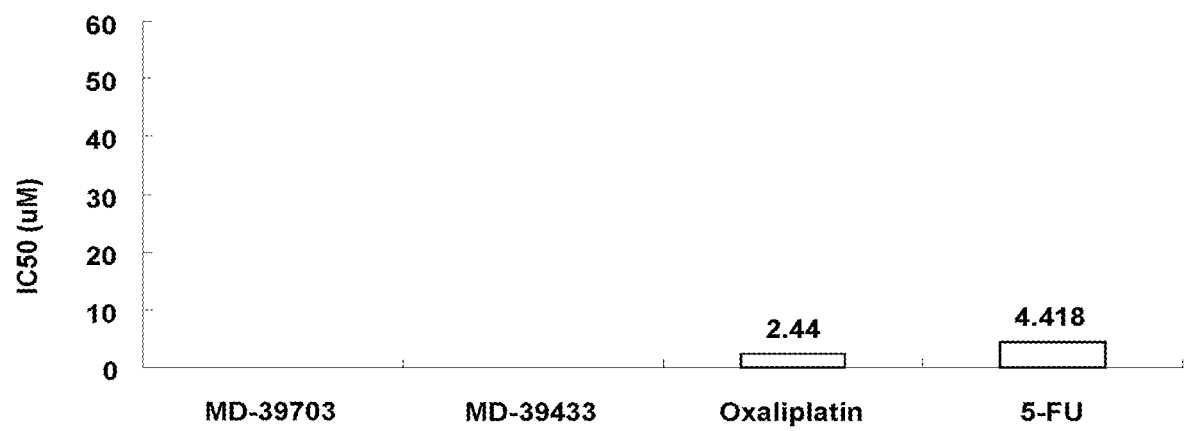
FIG. 7 shows the $IC_{50}$ values of MD-39703 and MD-39433 and the control chemicals oxaliplatin and 5-FU in fetal hepatocytes HL-7002.

HL-7002 hepatocyte cell line cells were treated with drugs (MD-39703, MD-39433, oxaliplatin, or 5-F U) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 7.

For HL-7002 cells, no toxicity was detected for MD-39703 and MD-39433. $IC_{50}$s of oxaliplatin and 5-FU were 2.44 μM and 4.418 μM, respectively (FIG. 7).

Figure 8:
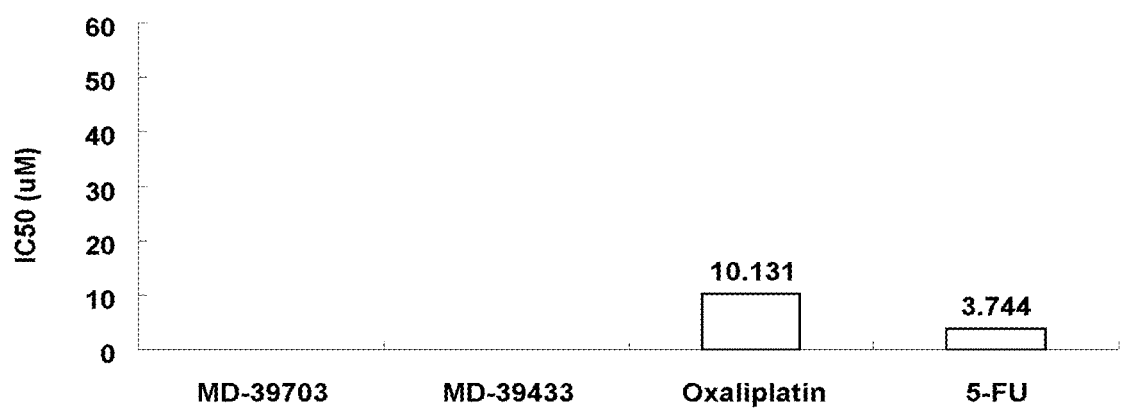
FIG. 8 shows the $IC_{50}$ values of MD-39703 and MD-39433 and the control chemicals oxaliplatin and 5-FU in human embryonic kidney cell line HEK293.

HEK293 kidney cell line cells were treated with drugs (MD-39703, MD-39433, oxaliplatin, or 5-FU) at step-wise concentrations, and the cell viability was evaluated with the CellTiter 96 AQueous One Solution Cell Proliferation Assay from Promega Corp. (Madison, Wis., USA). The index of cell growth repression ratio was obtained by comparing the OD490 data of treatment group to the negative control. The drug response rate $IC_{50}$ was calculated with the SPSS 16.0 system. The results are shown in FIG. 8.

For HEK293, no toxicity was detected for MD-39703 and MD-39433. $IC_{50}$s of oxaliplatin and 5-FU were 10.131 μM and 3.744 μM respectively (FIG. 8).

Methods and Strategies:

Cell culture: Colorectal cancer cell lines HCT-116 and HT29 were purchased from ATCC (Manassas, Va.). The fetal hepatocytes HL-7002 and human embryonic kidney cells HEK393 were purchased from ATCC. The cells were cultured in RPMI+5% Fetal Bovine Serum (FBS).

Drug treatment and cell viability (MTS) assay: The cells (105/100 mL/well) were cultured in a 96 well plate, and treated with drugs (e.g. MD-39703, MD-39433, oxaliplatin, or 5-FU) at step-wise concentrations from 0.01 to 300 μM. The cells treated with the solvents were used as the negative control, and cisplatin and docetaxel were used as the positive controls. The cells were monitored daily, and the cell viability was evaluated with the Promega CellTiter 96 AQueous One Solution Cell Proliferation Assay (Promega, Madison, Wis., USA) according to the manufacture manuals. The cell viability was monitored at OD490 reading in a bio-spectrometer (Perkin Elmer, Waltham, Mass., USA).

Data analysis: The OD490 reading data were collected hourly from 1 h to 4 h after the addition of lysis buffer. The index of cell growth repression ratio was obtained by comparing the OD490 data of treatment to the negative control. The drug response rate $IC_{50}$ was calculated with the SPSS 16.0.

Summary of Effects:

For colorectal cancer cell line HCT-116, MD-39703 and MD-39433 showed weaker but comparable toxicity than for oxaliplatin and 5-FU. For colorectal cancer cell line HT29, MD-39703 and MD-39433 showed a weaker but comparable toxicity than for oxaliplatin, and stronger toxcity than for 5-FU. For HL-7002, an immortalized human fetal hepatic cell line, MD-39703 and MD-39433 showed no toxicity. For HEK293, an immortalized human fetal kidney cell line, MD-39703 and MD-39433 showed no toxicity.

Process to Produce the Co-Crystals and their Characterizations

Each of the co-crystals of the current invention was formed from a platinum analogues and a diacid as co-crystal formers. The co-crystals were obtained by slurrying or grinding platinum analogues and diacids in no solvent or some solvent or mixture of solvents, or by treating the solution with one or more of several methods, e.g., stepwise heating and cooling the solution, evaporation of the co-crystal formers solution, freeze drying of the co-crystal formers solution, cooling and evaporation of the co-crystal formers solution.

Some crystalline polymorphic forms of the co-crystals of the present invention were first produced. Amorphous forms of the co-crystal and other forms may be existent using different methods such as but not limited to crystallization processes. Polymorphic forms of the co-crystal of platinum analogues were confirmed by X-Ray powder diffraction (XRPD), thermal gravimetric analysis (TGA) and differential scanning calorimetry (DSC), scanning electron microscopy (SEM), and other methods. Analysis of the co-crystals showed that each co-crystal contains one platinum analogue and the corresponding diacid in a 1:1 mol ratio. Different ratios of the platinum analogues and the acids may exist using different processes.

Some representative co-crystals with platinum analogues and diacids as co-crystal formers are listed in Table 7.

Experiment 1

Mixtures of 550 mg of carboplatin (Pt-01), 300 mg of cis-endo-5-Norbornene-2,3-dicarboxylic acid (CF-08) and 3.0 mL of distilled water were stirred around 30° C. for 5 hours. Then more distilled water was added to dissolve the mixtures. The obtained solution was filtered through a 0.45 um filter and the solution was dried by stepwise cooling. After cooling dry, the resulted crude crystal was treated with ethanol and heptane and 448 mg of pure crystal (MD-39551)

TABLE 7

Figure 9:
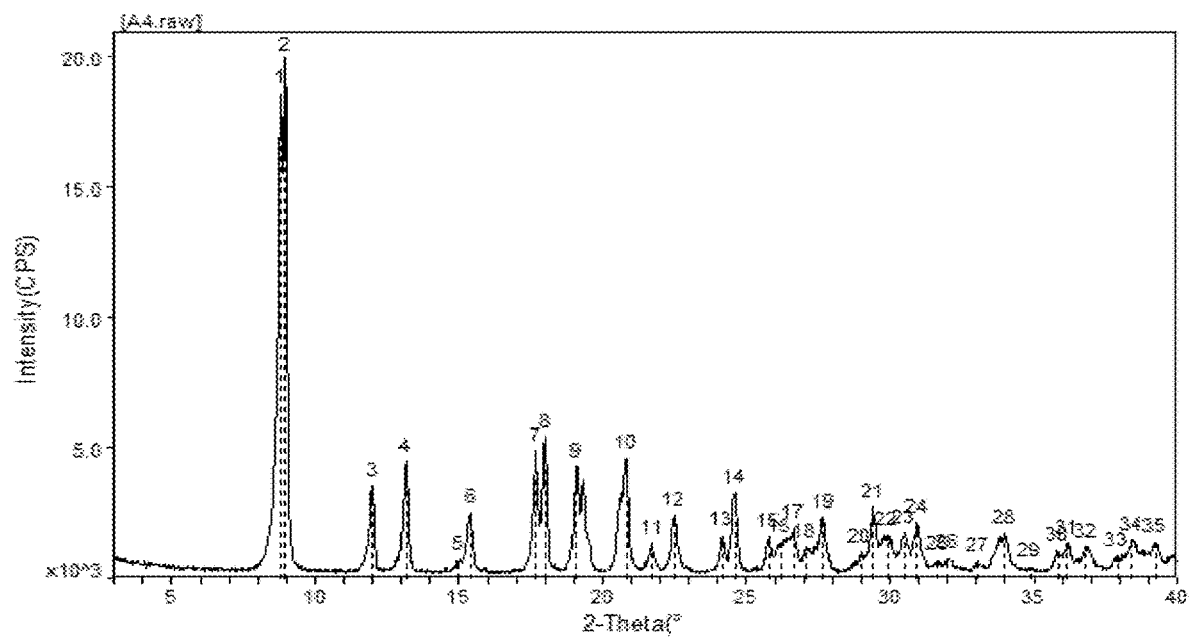
FIG. 9 shows an X-ray powder diffraction (XRPD) pattern of the co-crystal MD-36042.
Figure 10:
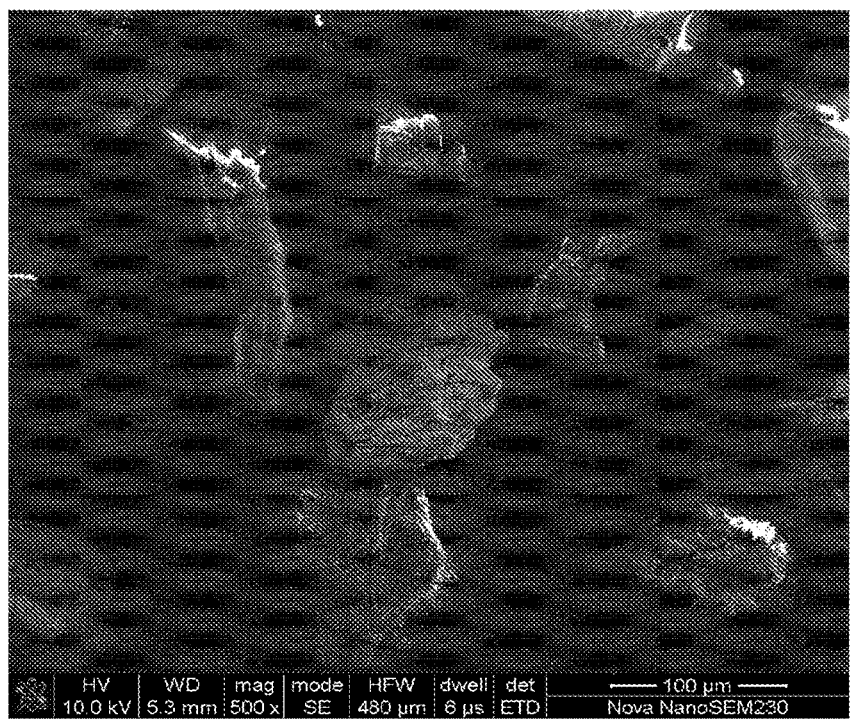
FIG. 10 shows a scanning electron microscope (SEM) image of the co-crystal MD-36042.
Figure 11:
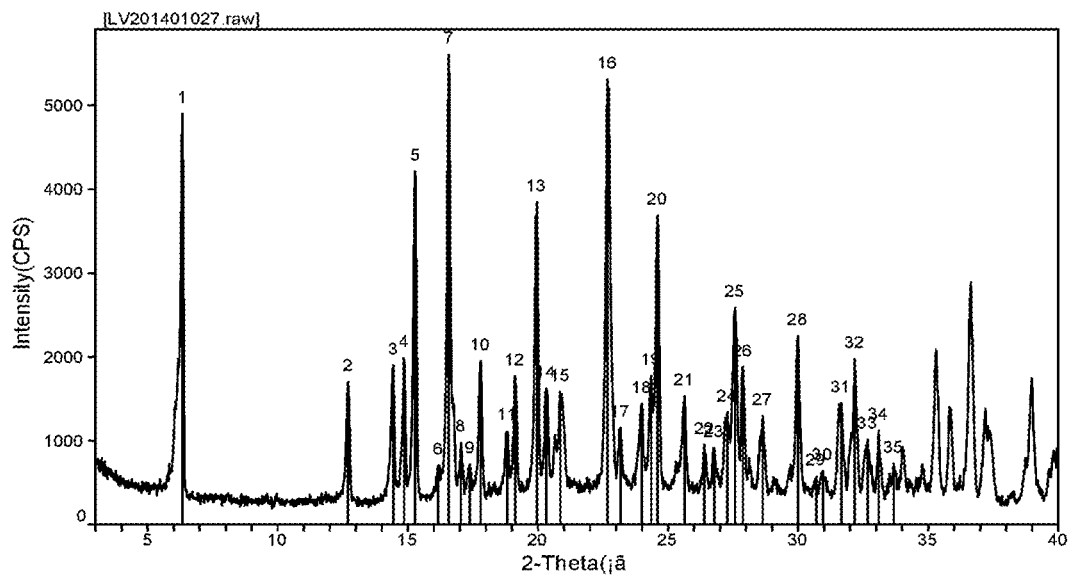
FIG. 11 shows an XRPD pattern of the co-crystal MD-39551.
Figure 12:
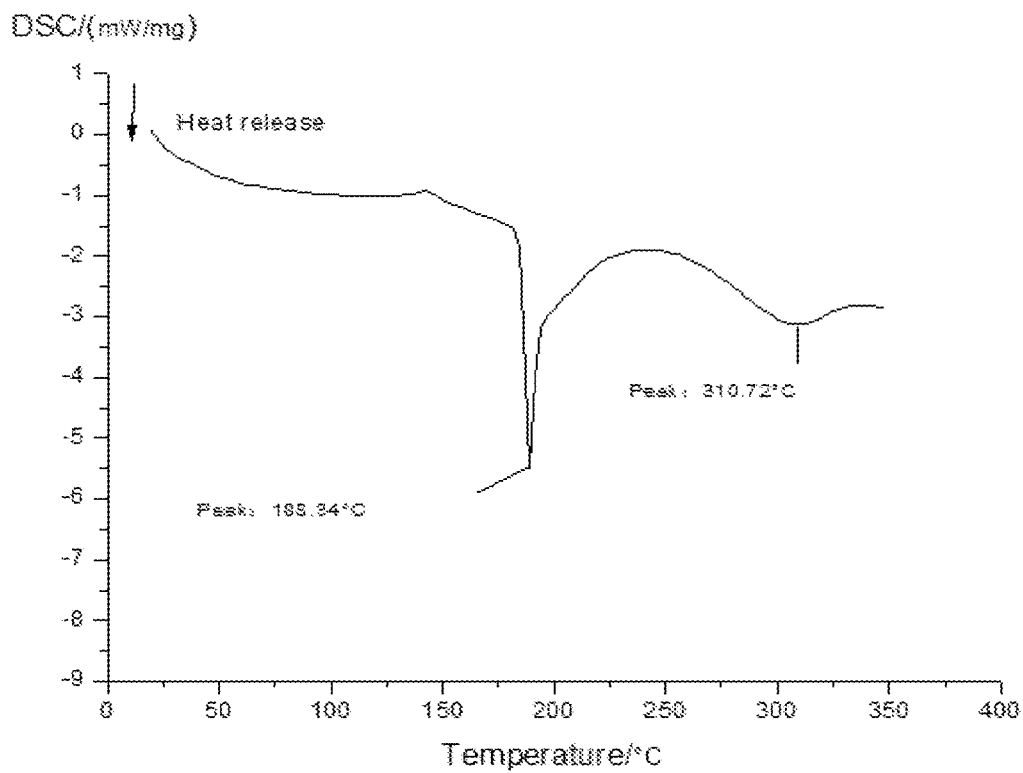
FIG. 12 shows a differential scanning calorimetry (DSC) result of the co-crystal MD-39551.
Figure 13:
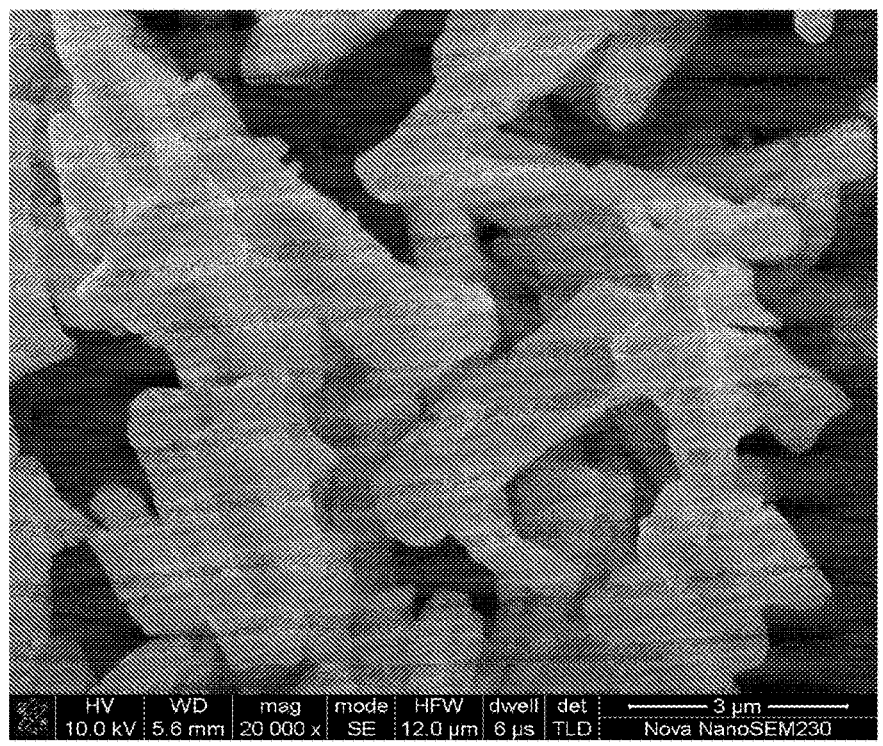
FIG. 13 shows a SEM image of the co-crystal MD-39551.
Figure 15:
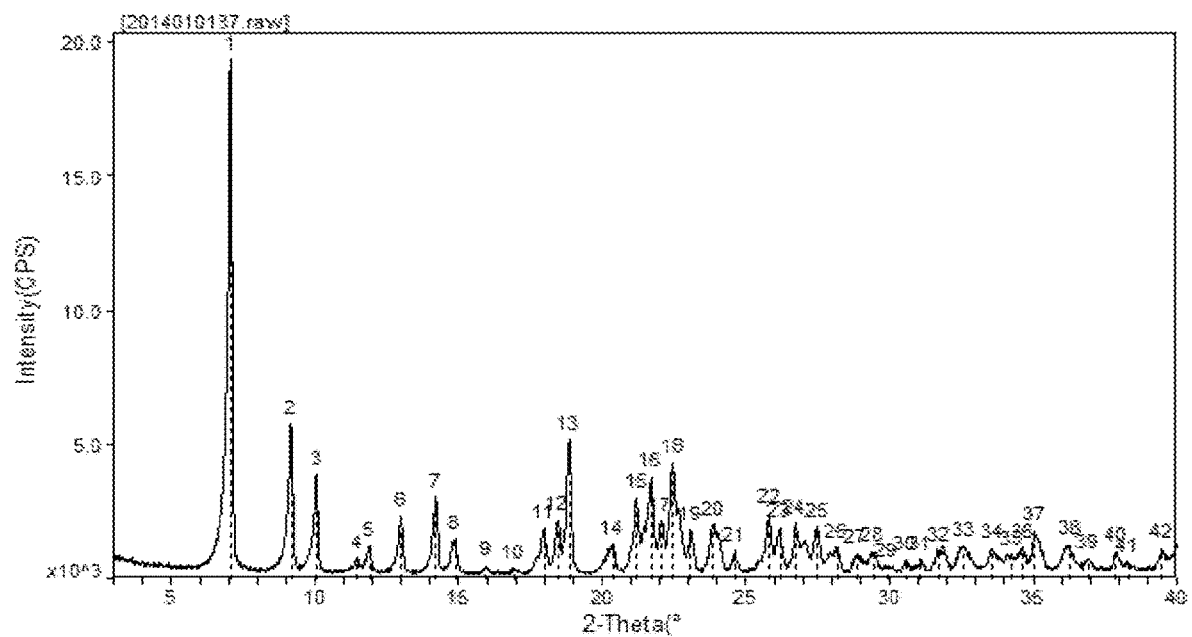
FIG. 15 shows an XRPD pattern of the co-crystal MD-39433.
Figure 16:
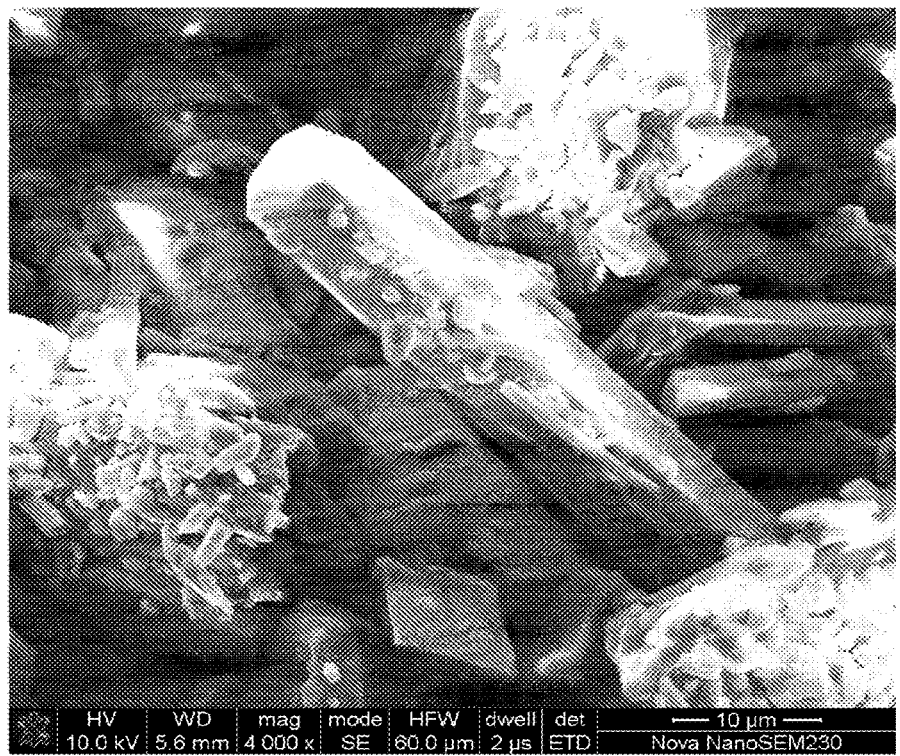
FIG. 16 shows a SEM image of the co-crystal MD-39433.
Figure 17:
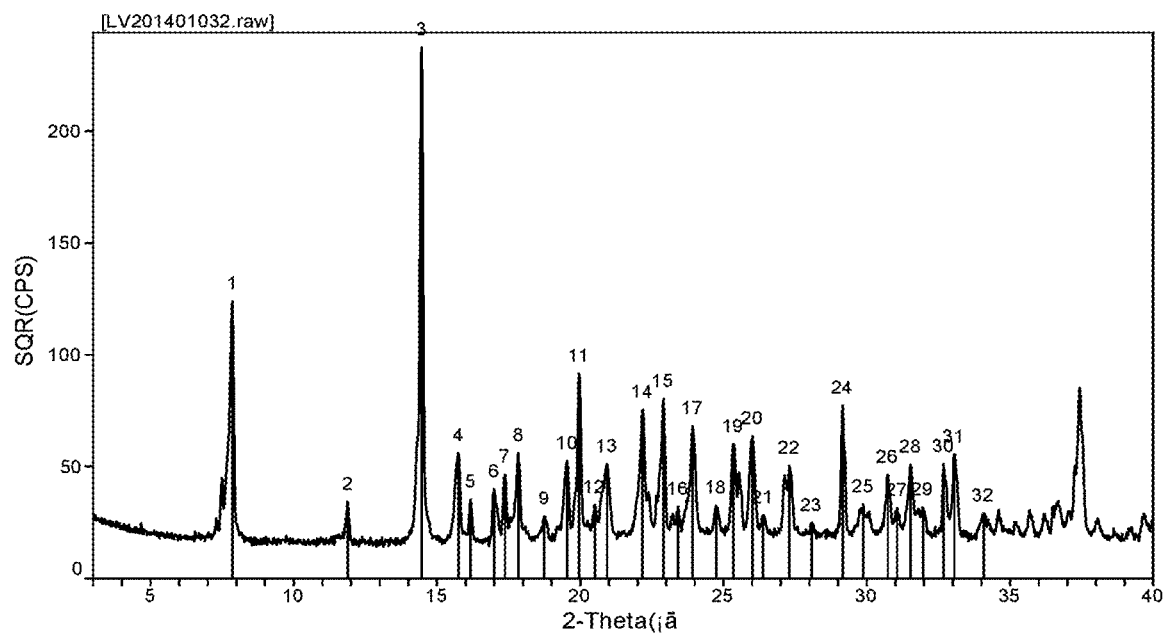
FIG. 17 shows an XRPD pattern of the co-crystal MD-39703.
Figure 18:
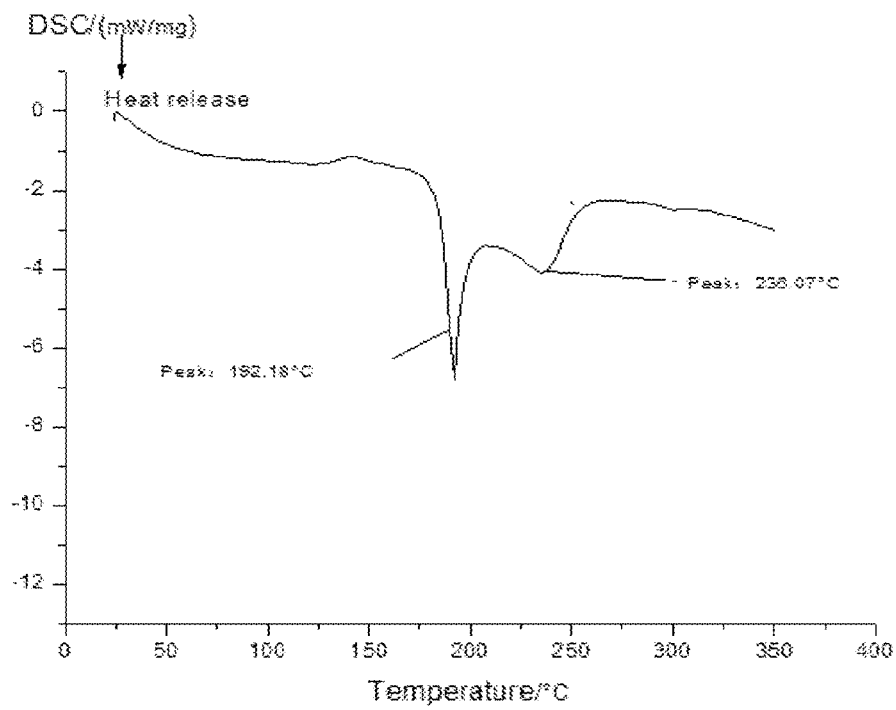
FIG. 18 shows a DSC result of the co-crystal MD-39703.
Figure 19:
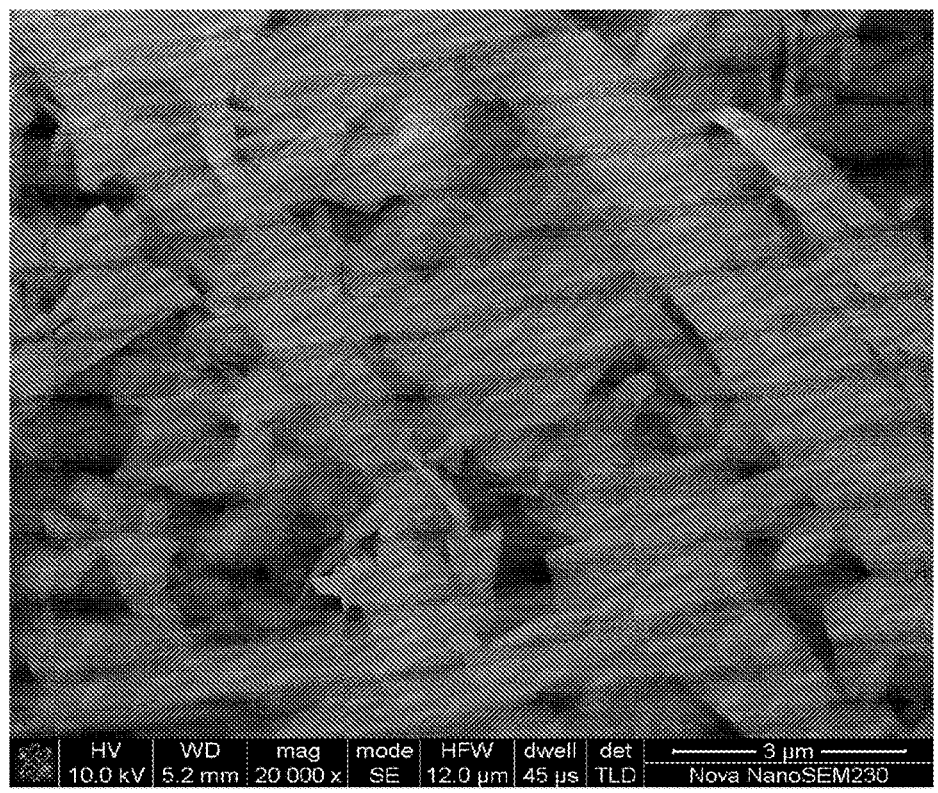
FIG. 19 shows a SEM image of the co-crystal MD-39703.

| Formula | Co-crystal number | Characterizations |
|---|---|---|
| [carboplatin · 1,1-cyclopropanedicarboxylic acid] | MD36042 | HPLC, MS, $^1$H-NMR<br>XRPD (FIG. 9); SEM (FIG. 10); |
| [carboplatin · cis-endo-5-norbornene-2,3-dicarboxylic acid] | MD39551 | HPLC, MS, $^1$H-NMR<br>XRPD (FIG. 11); DSC (FIG. 12); SEM (FIG. 13) |
| [oxaliplatin · 1,1-cyclobutanedicarboxylic acid] | MD39433 | HPLC, MS, $^1$H-NMR<br>XRPD (FIG. 15); SEM (FIG. 16) |
| [oxaliplatin · 1,1-cyclopropanedicarboxylic acid] | MD39442 | HPLC, MS, $^1$H-NMR<br>XRPD (FIG. 14) |
| [oxaliplatin · cis-endo-5-norbornene-2,3-dicarboxylic acid] | MD39703 | HPLC, MS, $^1$H-NMR<br>XRPD (FIG. 17); DSC (FIG. 18); SEM (FIG. 19) |
| [Pt(NH$_3$)$_2$(glycolate) · 1,1-cyclobutanedicarboxylic acid] | HP309 | HPLC, MS, $^1$H-NMR<br>XRPD (FIG. 20) |
| [spiroplatin analogue · 1,1-cyclobutanedicarboxylic acid] | MD3176 | HPLC, MS, $^1$H-NMR<br>XRPD (FIG. 21) | was obtained. Its characterization by XRPD, DSC/TGA and $^1$H-NMR confirmed the structure the same as indicated in the Table 6.

Experiment 2

Mixtures of 400 mg of lobaplatin (Pt-05 in Table 1), 400 mg of 1,1-cyclobutane dicarboxylate (CF-01 in Table 6) and 3.0 mL of distilled water were stirred around 30° C. for 5 hours. Then the reaction was cooled to 0-5° C. and stirred over 5 hours. The resulted crude crystal was obtained by filtering and was washed by cooling distilled water, ethanol and heptane. After dried in vacuum, and 417 mg of pure crystal was obtained. It was analyzed by HPLC, MS and $^1$H-NMR. The characterization indicated 1:1 ratio of lobaplatin to 1,1-cyclobutane dicarboxylate in this co-crystal (MD-3176) structure. Its characterization by XRPD, DSC/TGA and $^1$H-NMR confirmed the structure the same as indicated in the Table 6.

Experiment 3

Mixtures of 400 mg of lobaplatin (Pt-05 in Table 1), 520 mg of CF-10A (CF-10A in Table 6) and 3.0 mL of distilled water were stirred around 30° C. for 5 hours. Then the reaction was cooled to 0-5° C. and stirred over 5 hours. The resulted crude crystal was obtained by filtering and was washed by cooling distilled water, ethanol and heptane. After dried in vacuum, and 406 mg of pure crystal was obtained. It was analyzed by HPLC, MS and $^1$H-NMR. The characterization indicated 1:1 ratio of lobaplatin to 1,1-cyclobutane dicarboxylate in this co-crystal structure.

Experiment 4

Mixtures of 400 mg of lobaplatin (Pt-05 in Table 1), 532 mg of CF-10B (CF-10B in Table 6) and 3.0 mL of distilled water were stirred around 30° C. for 5 hours. Then the reaction was cooled to 0-5° C. and stirred over 5 hours. The resulted crude crystal was obtained by filtering and was washed by cooling distilled water, ethanol and heptane. After dried in vacuum, and 375 mg of pure crystal was obtained. It was analyzed by HPLC, MS and $^1$H-NMR. The characterization indicated 1:1 ratio of lobaplatin to 1,1-cyclobutane dicarboxylate in this co-crystal structure.

Experiment 5

Mixtures of 400 mg of lobaplatin (Pt-05 in Table 1), 540 mg of CF-10C (CF-10C in Table 6) and 3.0 mL of distilled water were stirred around 30° C. for 5 hours. Then the reaction was cooled to 0-5° C. and stirred over 5 hours. The resulted crude crystal was obtained by filtering and was washed by cooling distilled water, ethanol and heptane. After dried in vacuum, and 427 mg of pure crystal was obtained. It was analyzed by HPLC, MS and $^1$H-NMR. The characterization indicated 1:1 ratio of lobaplatin to 1,1-cyclobutane dicarboxylate in this co-crystal structure.

Experiment 6

Mixtures of 400 mg of lobaplatin (Pt-05 in Table 1), 540 mg of CF-10D (CF-10D in Table 6) and 3.0 mL of distilled water were stirred around 30° C. for 5 hours. Then the reaction was cooled to 0-5° C. and stirred over 5 hours. The resulted crude crystal was obtained by filtering and was washed by cooling distilled water, ethanol and heptane. After dried in vacuum, and 465 mg of pure crystal was obtained. It was analyzed by HPLC, MS and $^1$H-NMR. The characterization indicated 1:1 ratio of lobaplatin to 1,1-cyclobutane dicarboxylate in this co-crystal structure.

Experiment 7

Mixtures of 400 mg of lobaplatin (Pt-05 in Table 1), 550 mg of Lactic acid and 20.0 mL of distilled water were stirred around 30° C. for 5 hours. Then the obtained solution was filtered through 0.45 um filter and the solution was dried by stepwise cooling. After cooling dry, the resulted crude crystal was treated with ethanol and heptane and 355 mg of pure crystal was obtained. It was analyzed by HPLC, MS and $^1$H-NMR. The characterization indicated 1:1 ratio of lobaplatin to Lactic acid in this co-crystal structure.

Experiment 8

General procedure for the preparation of co-crystals based on 1,1-cyclobutane dicarboxylate (CF-01 in Table 6) as a co-crystal former with one platinum analogue from Pt-02, Pt-03, Pt-04, Pt-05, Pt-06, Pt-07, Pt-08, Pt-09, Pt-10, Pt-11, Pt-12, Pt-13, Pt-14, Pt-15, Pt-16, Pt-17, Pt-18, Pt-19, Pt-20, Pt-21, Pt-22, Pt-23, Pt-24, Pt-25, Pt-26, Pt-27, Pt-28, Pt-29, Pt-30, Pt-31, Pt-32, and Pt-33, Mixtures of 1.0 mmol of any one platin analogues, 400 mg of 1,1-cyclobutane dicarboxylate (CF-01 in Table 6) and 3.0 mL of distilled water are stirred around 30° C. for 5 hours. Then the reaction is cooled to 0-5° C. and stirred over 5 hours. The resulted crude crystal is obtained by filtering and washed by cooling distilled water, ethanol and heptane. After dried in vacuum, and the desired pure crystal is obtained. Some products are analyzed by XRPD, DSC, HPLC, MS and $^1$H-NMR. The characterization indicate 1:1 ratio of selected platin analogues to 1,1-cyclobutane dicarboxylate in this co-crystal structure.

Experiment 9

Mixtures of 859 mg of Pt-36 (Pt-31 in Table 5), 1.36 g of 1,1-cyclobutane dicarboxylate (CF-01 in Table 6) and 10.0 mL of distilled water were stirred around 20° C. for 10 hours. Then the reaction was cooled to 0-5° C. and stirred over 5 hours. The resulted crude crystal was obtained by filtering and was washed by cooling distilled water, ethanol and heptane. After dried in vacuum, and 1.15 g of pure crystal was obtained. It was analyzed by HPLC, MS and $^1$H-NMR. The characterization indicated 1:1 ratio of Pt-31 (Pt-31 in Table 5) to 1,1-cyclobutane dicarboxylate in this co-crystal structure.

Experiment 10

Mixtures of 400 mg of nedaplatin (Pt-03 in Table 1), 520 mg of phenylmalonic acid (CF-10A in Table 6) and 3.0 mL of distilled water were stirred around 30° C. for 5 hours. Then the reaction was cooled to 0-5° C. and stirred over 5 hours. The resulted crude crystal was obtained by filtering and was washed by cooling distilled water, ethanol and heptane. After dried in vacuum, and 470 mg of pure crystal was obtained. It was analyzed by HPLC, MS and $^1$H-NMR. The characterization indicated 1:1 ratio of nedaplatin to phenylmalonic acid in this co-crystal structure.

Experiment 11

Mixtures of 410 mg of Pt-06 (Pt-06 in Table 1), 600 mg of 1,1-cyclobutane dicarboxylate (CF-01 in Table 6) and 5.0 mL of toluene was stirred around 30° C. for 5 hours. Then the reaction was cooled to 0-5° C. and stirred over 5 hours. The resulted crude crystal was obtained by filtering and was washed by pre-cooled toluene, ethanol and heptane. After dried in vacuum, and 220 mg of pure crystal was obtained. It was analyzed by HPLC, MS and $^1$H-NMR. The characterization indicated 1:1 ratio of Pt-06 to 1,1-cyclobutane dicarboxylate in this co-crystal structure.

Experiment 12

Mixtures of 466 mg of Pt-28 (Pt-21 in Table 5), 520 mg of tartaric acid and 5.0 mL of distilled water was stirred around 30° C. for 5 hours. Then the reaction was cooled to 0-5° C. and stirred over 5 hours. The resulted crude crystal was obtained by filtering and was washed by pre-cooled distilled water, ethanol and heptane. After dried in vacuum, and 420 mg of pure crystal was obtained. It was analyzed by HPLC, MS and $^1$H-NMR. The characterization indicated 1:1 ratio of Pt-21 to tartaric acid in this co-crystal structure.

Experiment 13

Mixtures of 580 mg of Pt-32 (Pt-32 in Table 5), 720 mg of phenylmalonic acid (CF-10A in Table 5) and 7.0 mL of distilled water was stirred around 30° C. for 5 hours. Then the reaction was cooled to 0-5° C. and stirred over 5 hours. The resulted crude crystal was obtained by filtering and was washed by pre-cooled distilled water, ethanol and heptane. After dried in vacuum, and 437 mg of pure crystal was obtained. It was analyzed by HPLC, MS and $^1$H-NMR. The characterization indicated 1:1 ratio of Pt-32 to phenylmalonic acid in this co-crystal structure.

Experiment 14

Mixtures of 526 mg of Pt-33 (Pt-28 in Table 5), 520 mg of critic acid and 5.0 mL of distilled water was stirred around 30° C. for 5 hours. Then the reaction was cooled to 0-5° C. and stirred over 10 hours. The resulted crude crystal was obtained by filtering and was washed by pre-cooled distilled water, ethanol and heptane. The crude solid was purified by re-crystallization in water. After dried in vacuum, and 320 mg of pure crystal was obtained. It was analyzed by HPLC, MS and $^1$H-NMR. The characterization indicated 1:1 ratio of Pt-28 to critic acid in this co-crystal structure.

Experiment 15

Mixtures of 465 mg of Pt-21 (Pt-21 in Table 5), 522 mg of 1,2-cis-cyclobutane dicarboxylate (CF-04 in Table 6) and 5.0 mL of distilled water was stirred around 20° C. for 7 hours. Then the reaction was cooled to 0-5° C. and stirred over 10 hours. The resulted crude crystal was obtained by filtering and was washed by pre-cooled distilled water, ethanol and heptane. The crude solid was purified by re-crystallization in water. After dried in vacuum, and 458 mg of pure crystal was obtained. It was analyzed by HPLC, MS and $^1$H-NMR. The characterization indicated 1:1 ratio of Pt-21 to 1,2-cis-cyclobutane dicarboxylate in this co-crystal structure.

Analytical Methods

X-Ray Powder Diffraction (XRPD)

Polarized light microscopic picture was captured at room temperature (RT). X-ray intensity data were collected at 296(2) K using a Bruker APEX 11 CCD diffractometer (Mo Kα radiation, λ=0.71073 Å). XRPD pattern was collected by Panalytical Empyrean system at RT. Direct methods structure solution, difference Fourier calculations and full-matrix least-squares refinement against F2 were performed with SHELXTL and OLEX2, See Sheldrick G M. *Acta Crystallogr A*, 64: 112-122, 2008; and O. V. Dolomanov, et al. *J. Appl. Cryst.* 42, 339-341, 2009; and Brandenburg, K. DIAMOND, 1999, Crystal Impact GbR, Bonn, Germany. Molecular graphics were created according to Brandenburg, K. *DIAMOND,* 1999, Crystal Impact GbR, Bonn, Germany.

Analytical Instrument: Panalytical Empyrean. The X-ray powder diffraction was conducted by mounting a sample of the crystalline material on a Si single crystal low-background holder and spreading out the sample into a thin layer with the aid of a microscope slide. The 20 position was calibrated against Panalytical 640 Si powder standard. The sample was irradiated with X-rays generated by a copper long-fine focus tube operated at 45 kV and 40 mA with a wavelength of Kα1=1.540589 angstroms and Kα2=1.544426 angstroms (Kα2/Kα1 intensity ratio is 0.50). The collimated X-ray source was passed through a programmed divergence slit set at 10 mm and the reflected radiation directed through a 5.5 mm anti-scatter slit. The sample was exposed for 16.3 seconds per 0.013° 2-theta increment (continuous scan mode) over the range 3 degrees to 40 degrees 2-theta in theta-theta mode. The running time was 3 minutes and 57 seconds. The instrument was equipped with a RTMS detector (X'Celerator). Control and data capture was by means of a Dell Optiplex 780 XP operating with data collector software.

Persons skilled in the art of X-ray powder diffraction will realize that the relative intensity of peaks can be affected by, for example, grains above 30 microns in size and non-unitary aspect ratios that may affect analysis of samples. The skilled person will also realize that the position of reflections can be affected by the precise height at which the sample sits in the diffractometer and the zero calibration of the diffractometer. The surface planarity of the sample may also have a limited effect. Hence the diffraction pattern data presented are not intended to be limited to the absolute values.

Differential Scanning Calorimetry (DSC)

DSC was used as a thermoanalytical method to measure the difference in the amount of heat required to increase the temperature of a sample and reference was measured as a function of temperature. The general process of DSC is known and the specific instruments and conditions in the following Examples were as follows:
Analytical Instrument: TA Instruments Q2000 DSC;
Heating rate: 10° C. per minute; and Purge gas: nitrogen.

Thermal Gravimetric Analysis (TGA)

TGA was used to measure changes in physical and chemical properties of samples as a function of increasing temperature (with constant heating rate), or as a function of time (with constant temperature and/or constant mass loss). The general process of TGA is known and the specific instruments and conditions in the following Examples were as follows:
Analytical Instrument: TA Instruments Q5000 TGA;
Heating rate: 10° C. per minute; and
Purge gas: nitrogen.

Sample Pharmaceutical Composition and its Administration

Aqueous or solid pharmaceutical composition of the present invention comprises an effective amount of the co-crystal of the current invention, e.g. MD39551, with or without an appropriate amount of at least one additional therapeutic agent or adjuvant therapy agent. The co-crystal, as well as the therapeutic agent or adjuvant therapy agent, may be dissolved or dispersed in a pharmaceutical acceptable carrier or aqueous media.

Depending on the particular cancer to be treated, administration of pharmaceutical composition according to the present invention can via any common route as long as the target issue is available via the route. For example, the pharmaceutical composition may be administered by infusion, injection, or via the oral route.

A number of pharmaceutical compositions were produced:

Pharmaceutical composition sample A: 70 g of MD-39551 was dissolved in pre-treated normal saline or 5% of aqueous glucose (in water) and the final volume of the solution was adjusted to 5.0 L. Then the solution was filtered through 0.22 um filter and dispersed into ample bottles with 50.0 mL in each.

What is claimed is:

1. A co-crystal comprising a platinum analogue of formula Pt-02:

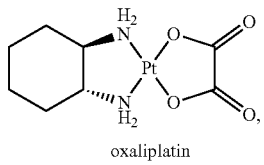

oxaliplatin

Pt-02 and a diacid selected from the group consisting of:

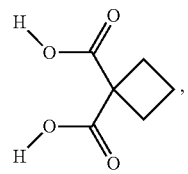

CF-01

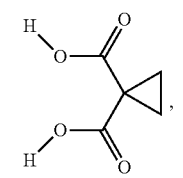

CF-02

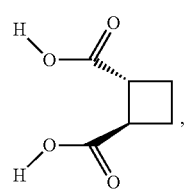

CF-03

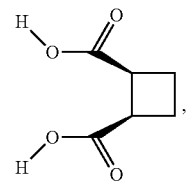

CF-04

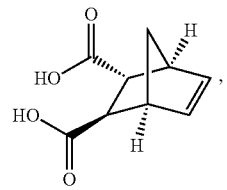

CF-08

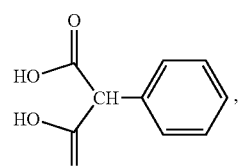

CF-10A

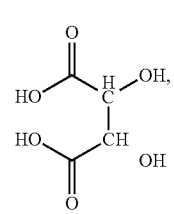

CF-10B

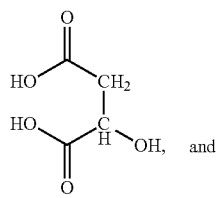

CF-10C

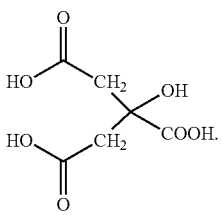

CF-10D

2. The co-crystal of claim 1, wherein the diacid is selected from the group consisting of formulas CF-01, CF-02, and CF-08.

3. The co-crystal of claim 1, which is a co-crystal comprising the platinum analogue of formula Pt-02 and the diacid of formula CF-02 and having an XRPD pattern comprising peaks at diffraction angles 2-Theta of 7.3°, 9.4°, 10.1°, 12.5°, 13.6° and 23.4°±0.2; or a co-crystal comprising the platinum analogue of formula Pt-02 and the diacid of formula CF-08 and having an XRPD pattern comprising peaks at diffraction angles 2-Theta of 7.9°, 11.9°, 14.5°, 15.8°, 17.0°, 17.4° and 17.8°±0.2.

4. The co-crystal of claim 1, which is a co-crystal comprising the platinum analogue of formula Pt-02 and the diacid of formula CF-01 and having an XRPD pattern comprising peaks at diffraction angles 2-Theta of 7.1°, 9.2°, and 10.1°±0.2.

5. The co-crystal of claim 1, which is a co-crystal comprising the platinum analogue of formula Pt-02 and the diacid of formula CF-08 and having an XRPD pattern substantially similar to the pattern as set forth in FIG. 17.

6. A pharmaceutical composition comprising the co-crystal of claim 1.

7. A pharmaceutical composition comprising the co-crystal of claim 3.

8. A pharmaceutical composition comprising the co-crystal of claim 4.

9. A pharmaceutical composition comprising the co-crystal of claim 5.

10. An aqueous pharmaceutical composition prepared by dissolving or dispersing the co-crystal of claim 1 in an aqueous media.

11. The pharmaceutical composition of claim 6, further comprising a therapeutic agent or adjuvant therapy agent selected from the group consisting of folic acid, coenzyme Q10, curcumin, glutathione (GSH), aloe vera, oryzanol, 5-fluorouracil, and bortezomib.

12. A method of treating cancer in a subject in need thereof, comprising administering to the subject the pharmaceutical composition of claim 6, wherein the co-crystal is in a therapeutically effective amount, wherein the treating (i) reduces the appearance of the cancer, (ii) reduces the symptoms of the cancer, and/or (iii) slows, halts, or reverses the progression of the cancer.

13. A method of treating cancer in a subject in need thereof, comprising administering to the subject the pharmaceutical composition of claim 8, wherein the co-crystal is in a therapeutically effective amount, wherein the treating (i) reduces the appearance of the cancer, (ii) reduces the symptoms of the cancer, and/or (iii) slows, halts, or reverses the progression of the cancer.

14. A method of treating cancer in a subject in need thereof, comprising administering to the subject the pharmaceutical composition of claim 9, wherein the co-crystal is in a therapeutically effective amount, wherein the treating (i) reduces the appearance of the cancer, (ii) reduces the symptoms of the cancer, and/or (iii) slows, halts, or reverses the progression of the cancer.

15. The method of claim 12, wherein the cancer is prostate cancer, colorectal cancer, or renal adenocarcinoma.

16. A method of preparing a co-crystal comprising:
a) mixing a platinum analogue and a diacid in water,
b) slurrying or stirring the mixture from step a) for a sufficient period of time to form a co-crystal of the platinum analog and the diacid; and optionally
c) isolating the co-crystal,
wherein the platinum analog is a platinum analogue of formula Pt-02:

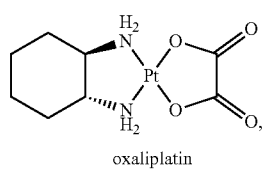

oxaliplatin

Pt-02 and the diacid is selected from the group consisting of:

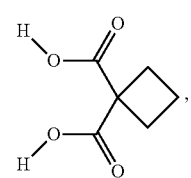

CF-01

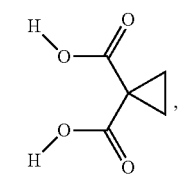

CF-02

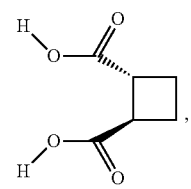

CF-03

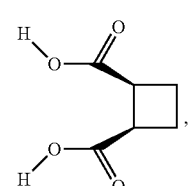

CF-04

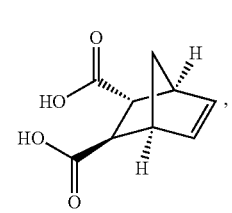

CF-08

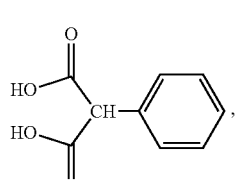

CF-10A

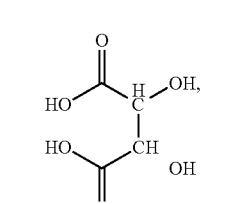

CF-10B

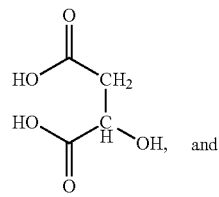

CF-10C and

-continued
CF-10D
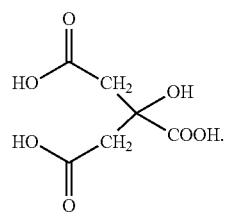
17. The method of claim 16, wherein the molar ratio of the platinum analogue to the diacid is in range of 1:0.1 to 1:20.
18. The method of claim 17, wherein the diacid is CF-01.
19. The co-crystal produced by the method of claim 16.
20. The co-crystal produced by the method of claim 18.
* * * * *